United States Patent
Ziegler et al.

(10) Patent No.: US 6,313,166 B1
(45) Date of Patent: Nov. 6, 2001

(54) PHENYL ACETIC ACID DERIVATIVES AS PESTICIDES

(75) Inventors: Hugo Ziegler, Witterswil (CH); Stephan Trah, Freiburg (DE); Saleem Farooq, Arisdorf; René Zurflüh, Basel, both of (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/338,236

(22) Filed: Jun. 22, 1999

Related U.S. Application Data

(63) Continuation of application No. 08/968,143, filed on Nov. 12, 1997, now Pat. No. 5,981,585, which is a continuation of application No. 08/526,859, filed on Sep. 11, 1995, now Pat. No. 5,756,426, which is a continuation-in-part of application No. 08/367,964, filed on Jan. 3, 1995, now abandoned.

(30) Foreign Application Priority Data

Jan. 5, 1994 (SZ) ...................................... 12/94-9
Jul. 1, 1994 (SZ) .................................. 2117/94-0

(51) Int. Cl.$^7$ ................ A01N 37/34; A01N 37/44; C07C 229/00; C07C 255/00
(52) U.S. Cl. .................... 514/539; 514/538; 514/563; 560/35; 560/42; 564/149; 564/168; 504/312
(58) Field of Search ............ 560/35, 42; 564/149, 564/168; 514/538, 539, 563

(56) References Cited

U.S. PATENT DOCUMENTS 5,387,607 * 2/1995 Brand et al. ..................... 514/513

FOREIGN PATENT DOCUMENTS

2005345 * 6/1990 (CA).

* cited by examiner

Primary Examiner—Laura L. Stockton
(74) Attorney, Agent, or Firm—Joseph C. Gil

(57) ABSTRACT

Compounds of the formula I

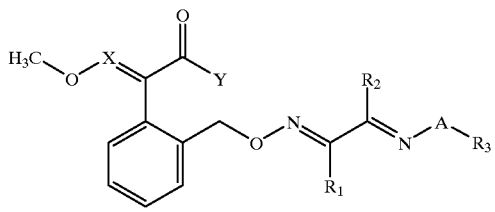

and the isomers thereof, in which either a) X is an N atom and
Y is $OR_{11}$ or $N(R_{12})R_{13}$, or b) X is CH and
Y is $OR_{11}$, and in which furthermore:

$R_{11}$ is $C_1$–$C_4$ alkyl;

$R_{12}$ and $R_{13}$, independenty, are hydrogen or $C_1$–$C_4$ alkyl;

A is an O atom or the group $NR_4$; and wherein $R_1$, $R_2$ and $R_3$ are as defined herein, are pesticidal active ingredients.

They can be used for pest control, in particular as microbicides, insecticides and acaricides in agriculture, horticulture and in the hygiene sector.

52 Claims, No Drawings

PHENYL ACETIC ACID DERIVATIVES AS PESTICIDES

CROSS-REFERENCE TO RELATED APPLICATIONS

This is a continuation of Ser. No. 08/968,143 filed Nov. 12, 1997, now U.S. Pat. No. 5,981,585, issued Nov. 9, 1999, which in turn is a continuation of Ser. No. 08/526,859, filed Sep. 11, 1995, now U.S. Pat. No. 5,756,426, which in turn is a continuation-in-part of Ser. No. 08/367,964, filed Jan. 3, 1995, now abandoned.

DETAILED DESCRIPTION

The invention relates to novel pesticidally active compounds of the formula I

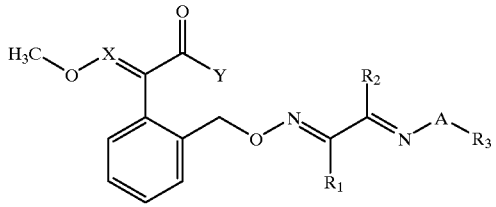

and to the isomers, and isomer mixtures, thereof which are possible, in which either
  a) X is an N atom and
     Y is $OR_{11}$ or $N(R_{12})R_{13}$, or
  b) X is CH and
     Y is $OR_{11}$,
and in which furthermore:
$R_{11}$ is $C_1-C_4$alkyl;
$R_{12}$ and $R_{13}$, independently, are hydrogen or $C_1-C_4$alky;
A is an O atom or the group $NR_4$;
$R_1$ is hydrogen, $C_1-C_4$alkyl, halo-$C_1-C_4$alkyl, cyclopropyl, cyano or methylthio;
$R_2$ is hydrogen, $C_1-C_6$alkyl, $C_3-C_6$cycloalkyl, a group

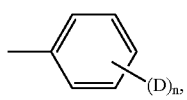

a group

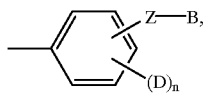

or thienyl;
D radicals are identical or different and are halogen, $C_1-C_4$alkyl, $C_1-C_4$alkoxy, $C_1-C_2$haloalkyl, $C_1-C_2$haloalkoxy, $C_3-C_6$alkenyloxy, $C_3-C_6$alkynyloxy, $C_1-C_4$alkylenedioxy, cyano or nitro;
n is 0, 1, 2, 3 or 4;
Z is $-O-$, $-O-(C_1-C_4$alkyl$)-$, $-(C_1-C_4$alkyl$)-O-$, $-S(O)_m-$, $-(C_1-C_4$alkyl$)-S(O)_m-$, $-S(O)_m-(C_1-C_4$alkyl$)-$,
m is 0, 1 or 2,
B is $C_1-C_6$alkyl, halo-$C_1-C_6$alkyl, $C_3-C_6$cycloalkyl or is $C_2-C_6$alkenyl or $C_2-C_4$alkynyl-$C_1-C_2$alkyl, each of which is unsubstituted or substituted by 1 to 3 halogen atoms, or is aryl or heterocyclyl, each of these two, independently, being unsubstituted or mono- to pentasubstituted by $C_1-C_6$alkyl, halo-$C_1-C_6$alkyl, halogen, $C_1-C_6$alkoxy or
halo-$C_1-C_6$alkoxy, or a group

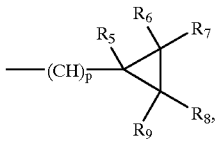

or trimethysily;
$R_5$, $R_6$, $R_7$, $R_8$ and $R_9$, independently, are hydrogen, $C_1-C_4$alkyl or halogen and p is 0, 1, 2 or 3;
$R_3$ is hydrogen, $C_1-C_6$alkyl, $C_1-C_6$haloalkyl having 1 to 5 halogen atoms, $C_1-C_4$alkoxy-$C_1-C_2$alkyl, $C_2-C_4$alkenyl-$C_1-C_2$akyl, which is unsubstituted or substituted by 1 to 3 halogen atoms, $C_2-C_4$alkynyl-$C_1-C_2$-alkyl, $C_3-C_6$cycloalkyl which is unsubstituted or substituted by 1 to 4 halogen atoms, $C_3-C_6$-cycloalkyl-$C_1-C_4$alkyl which is unsubstituted or substituted by 1 to 4 halogen atoms, cyano-$C_1-C_4$alkyl; $C_1-C_4$alkoxycarbonyl-$C_1-C_2$alkyl, $C_1-C_4$alkoxycarbamoyl-$C_1-C_2$alkyl, phenyl-$C_1-C_3$alkyl which is unsubstituted or substituted by halogen, $C_1-C_3$alkyl, $C_1-C_4$alkoxy, $C_1-C_4$haloalkyl, cyano, nitro or $C_1-C_4$alkylenedioxy, it being possible for the phenyl group to be monosubstituted to trisubstituted by identical or different substituents; phenyl which is unsubstituted or mono- to disubstituted, independently, by $C_1-C_4$alkyl, $C_1-C_4$alkoxy, halogen, $C_1-C_2$haloalkyl having 1 to 3 halogen atoms, nitro or cyano, or pyridyl which is unsubstituted or mono- to disubstituted, independently, by $C_1-C_4$alkyl, $C_1-C_4$alkoxy, halogen, $C_1-C_2$haloalkyl having 1 to 3 halogen atoms, nitro or cyano;
$R_4$ is $C_1-C_4$alkyl, phenyl, or
$R_3$ and $R_4$ together with the nitrogen atom to which they are bonded form a saturated or unsaturated 5- to 7-membered ring which is unsubstituted or substituted by $C_1-C_4$alkyl and which can have 1 to 3 additional hetero atoms selected from amongst N, O and S.

The compounds according to the invention have fungicidal, acaricidal and insecticidal properties and are suitable as active ingredients for use in agriculture, horticulture and the hygiene field.

The invention furthermore also relates to a process for the preparation of the compounds according to the invention, and to fungicidal, acaricidal and insecticidal compositions which comprise such compounds as active ingredients, and to the use of such compounds and compositions for controlling phytopathogenic fungi, Acarina and insects and for preventing such an attack.

If asymmetric carbon atoms exist in the compounds of the formula I, the compounds exist in optically active form. The compounds exist in any case in [E] and/or [Z] forms, merely because of the presence of the aliphatic, the oximino and the hydrazono double bonds. Furthermore, atropisomerism may exist The formula I is intended to embrace all these isomeric forms which are possible and their mixtures, for example racemic mixtures, and any [E/Z] mixtures.

Unless otherwise defined, the general terms used hereinabove and hereinbelow are intended to mean the following:

Halogen is fluorine, chlorine, bromine or iodine, in particular fluorine, chlorine or bromine, especially fluorine or chlorine.

Alkyl is either straight-chain, for example methyl, ethyl, n-propyl, n-butyl, n-hexyl, n-octyl, ndecyl, ndodecyl, n-hexadecyl or n-octadecyl, or branched, for example isopropyl, isobutyl, sec-butyl, tert-butyl, isopentyl, neopentyl or isohexyl.

Alkenyl is straight-chain or branched alkenyl, for example vinyl, 1-methylvinyl, allyl, 1-butenyl, isopropenyl, in particular allyl.

Alkynyl is, for example, ethynyl, 1-propynyl or 1-butynyl, in particular propargyl.

Cycloalkyl is to be understood as meaning cyclopropyl, cyclobutyl, cyclopentyl or cyclohexyl.

Halogen-substituted groups such as haloalkyl and haloalkoxy can be partially or fully halogenated by identical or different substituents. Examples of haloalkyl are methyl which is mono- to trisubstituted by fluorine, chlorine and/or bromine, such as $CHF_2$, $CF_3$ or $CH_2Cl$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ or $CClFCHClF$; trifluoromethyl is very particularly preferred.

Straight-chain $C_1$–$C_4$alkylenedioxy is —O—$CH_2$—O—, —O—$CH_2CH_2$—O—, —O—$CH_2CH_2CH_2$—O— or —O—$CH_2CH_2CH_2CH_2$—O—.

Aryl is, for example, phenyl or naphthyl in particular phenyl.

Heterocyclyl is a 5- to 7-membered aromatic or non-aromatic ring having one to three hetero atoms selected from the group consisting of N, O and S. Preferred are aromatic 5-and 6membered rings which have a nitrogen atom as hetero atom and, if appropriate, a further hetero atom, preferably nitrogen or sulfur, in particular nitrogen.

The term of the 5- to 7-membered ring which is formed by $R_3$ and $R_4$ together with the nitrogen atom to which they are bonded encompasses, in particular, pyrrolidine, piperidine, morpholine, thiomorpholine, hexamethyleneimine, imidazole, pytazole, pyrrole, 1,2,4-triazole, 1,2,3-triazole, tetrazole, isoxazole, oxazole, isoxazolidine, oxazolidine, thiazole, isothiazole, thiazoline and isothiazolidine.

Preferred within the scope of the invention are
(1) Compounds of the formula I in which either
  a) X is an N atom and
     Y is $OCH_3$ or $NHCH_3$, or
  b) X is CH and
     Y is $OCH_3$,
and in which furthermore:
  A is an O atom or the group $NR_4$;
  $R_1$ is hydrogen, $C_1$–$C_4$alkyl, halo-$C_1$–$C_4$alkyl, cyclopropyl, cyano or methylthio;
  $R_2$ is hydrogen, $C_1$–$C_6$alkyl, $C_3$–$C_6$cycloalkyl, a group

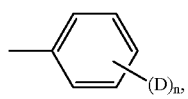

a group

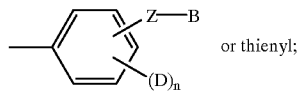 or thienyl;

D radicals are identical or different and are halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano or nitro;
  n is 0, 1, 2, 3 or 4;
  Z is —O—, —O—($C_1$–$C_4$alkyl)—, —($C_1$–$C_4$alkyl)—O—, —$S(O)_m$—, —($C_1$–$C_4$alkyl)—$S(O)_m$—, —$S(O)_m$—($C_1$–$C_4$alkyl)—;
  m is 0, 1 or 2;
  B is $C_1$–$C_6$alkyl, halo-$C_1$–$C_6$alkyl, $C_3$–$C_6$cycloalkyl, or is $C_2$–$C_6$alkenyl or $C_2$–$C_4$alkynyl-$C_1$–$C_2$alkyl, each of which is unsubstituted or substituted by 1 to 3 halogen atoms, or is aryl or heterocyclyl, or aryl or heterocyclyl, each of these, independently, being monosubstituted to pentasubstituted by $C_1$–$C_6$alkyl, halo-$C_1$–$C_6$alkyl, halogen, $C_1$–$C_6$alkoxy or halo-$C_1$–$C_6$alkoxy, or a group

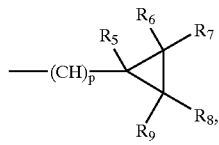

$R_5$, $R_6$, $R_7$, $R_8$ and $R_9$, independently, are hydrogen, $C_1$–$C_4$alkyl or halogen and p is 0, 1, 2 or 3;
  $R_3$ is hydrogen, $C_1$–$C_6$alkyl, $C_1$–$C_6$haloalkyl having 1 to 5 halogen atoms, $C_1$–$C_4$alkoxy-$C_1$–$C_2$alkyl, $C_2$–$C_4$alkenyl-$C_1$–$C_2$alkyl which is unsubstituted or substituted by 1 to 3 halogen atoms, $C_2$–$C_4$alkynyl-$C_1$–$C_2$alkyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano-$C_1$–$C_4$alkyl; $C_1$–$C_4$alkoxycarbonyl-$C_1$–$C_2$alkyl, phenyl-$C_1$–$C_3$alkyl which is unsubstituted or substituted by halogen, $C_1$–$C_3$alkyl, $C_1$–$C_4$alkoxy, $C_1$–$C_4$haloalkyl, cyano, nitro, $C_1$–$C_4$alkylenedioxy, it being possible for the phenyl group to be monosubstituted to trisubstituted by identical or different substituents; phenyl which is unsubstituted or mono- to disubstituted, independently, by $C_1$–$C_4$alkyl, $C_1$–$C_4$alkoxy, halogen, $C_1$–$C_2$haloalkyl having 1 to 3 halogen atoms, nitro or cyano, or pyridyl which is unsubstituted or mono- to disubstituted, independently, by $C_1$–$C_4$alkyl, $C_1$–$C_4$alkoxy, halogen, $C_1$–$C_2$haloalkyl having 1 to 3 halogen atoms, nitro or cyano;
  $R_4$ is $C_1$–$C_4$alkyl or phenyl, or
  $R_3$ and $R_4$ together with the nitrogen atom to which they are bonded form a saturated or unsaturated 5- to 7-membered ring which is unsubstituted or substituted by $C_1$–$C_4$alkyl and which can have 1 to 3 additional hetero atoms selected from amongst N, O and S;
(2) compounds of the formula I in which X is N and Y is $OCH_3$;
(3) compounds of the formula I in which X is CH;
(4) compounds of the formula I in which X is N, Y is $NHCH_3$ and $R_1$ is H, $CH_3$, cyclopropyl or CN;

(5) compounds of the formula I in which A is oxygen, NCH$_3$ or n-C$_6$H$_5$, in particular oxygen or NCH$_3$, very particularly oxygen;

(6) compounds of the formula I in which R$_1$ is hydrogen, methyl, cyclopropyl or cyano, in particular methyl;

(7) compounds of the formula I in which R$_2$ is C$_1$–C$_4$alkyl or cyclopropyl in particular methyl or cyclopropyl;

(8) compounds of the formula I in which R$_2$ is a group

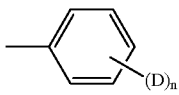

and

D is halogen, C$_1$–C$_4$alkyl, C$_1$–C$_4$alkoxy, C$_1$–C$_2$alkyl which is substituted 1 to 5 halogen atoms, C$_1$–C$_2$haloalkoxy, C$_3$–C$_6$alkenyloxy, C$_3$–C$_6$alkynyloxy, C$_1$–C$_4$alkylenedioxy, cyano, or nitro, or thienyl, D is, in particular, fluorine, chlorine, bromine, C$_1$–C$_4$alkyl or —CF$_3$;

(9) compounds of the formula I in which R$_2$ is a group

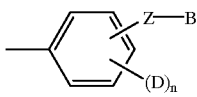

and

Z is —O—, —O—(C$_1$–C$_4$alkyl)—, —(C$_1$–C$_4$alkyl)—O—, —S(O)$_2$—, —(C$_1$–C$_4$alkyl)—S(O)$_2$—, —S(O)$_2$—(C$_1$–C$_4$alkyl)—, in particular —O—, —CH$_2$—O— or —O—CH$_2$—, very particularly —O—CH$_2$;

(10) compounds of the formula I in which R$_2$ is a group

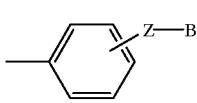

and

B is C$_1$–C$_4$alkyl, halogen-C$_1$–C$_4$alkyl, or is C$_2$–C$_4$alkenyl or C$_2$–C$_4$alkynyl-C$_1$–C$_2$alkyl, each of which is unsubstituted or substituted by 1 to 3 halogen atoms, or is aryl or aryl which is monosubstituted or disubstituted, independently, by C$_1$–C$_2$alkyl, halo-C$_1$–C$_2$alkyl, halogen, C$_1$–C$_2$alkoxy or halo-C$_1$–C$_2$alkoxy, or is a group

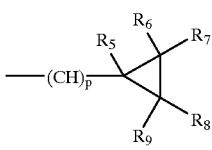

R$_5$, R$_6$, R$_7$, R$_8$ and R$_9$, independently, are hydrogen, C$_1$–C$_2$alkyl or halogen, and p is 0, 1, 2 or 3;

B is, in particular, C$_1$–C$_2$alkyl, halo-C$_1$–C$_3$alkyl, or is allyl or propargyl, each of which is unsubstituted or in each case substituted by 1 or 2 halogen atoms or 1 or two methyl groups, or phenyl, phenyl which is substituted by a substituent selected from the group consisting of fluorine, chlorine, bromine and CF$_3$, or a group

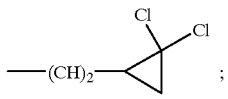

(11) compounds of the formula I in which R$_2$ is a phenyl group which is substituted in the 4-position by —Z—B;

(12) compounds of the formula I in which

R$_3$ is hydrogen, C$_1$–C$_6$alkyl or C$_1$–C$_4$haloalkyl having 1 to 3 halogen atoms, C$_1$–C$_2$alkoxy-C$_1$–C$_2$alkyl, C$_1$–C$_4$alkoxycarbonyl-C$_1$–C$_2$alkyl, propenyl which is unsubstituted or substituted by 1 to 3 halogen atoms, propargyl, C$_3$–C$_6$cycloalkyl, cyclopropylmethyl which is unsubstituted or substituted by 1 to 2 halogen atoms, cyano-C$_1$–C$_2$alkyl, phenyl-C$_1$–C$_2$alkyl which is unsubstituted or substituted by halogen, methyl, methoxy or halomethyl having 1 to 3 halogen atoms, it being possible for the phenyl group to be monosubstituted to disubstituted by identical or different substituents; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro; or R$_3$ and R$_4$ together with the nitrogen atom to which they are bonded form a saturated or unsaturated 5- to 7-membered ring which is unsubstituted or substituted by C$_1$–C$_4$alkyl and which can have 1 to 3 additional hetero atoms selected from amongst N, O and S;

R$_3$ is preferably hydrogen, C$_1$–C$_6$alkyl, C$_1$–C$_4$haloalkyl having 1 to 3 halogen atoms, C$_1$–C$_2$alkoxymethyl, prop-2-en-1-yl which is unsubstituted or substituted by 1 to 3 halogen atoms, propargyl, C$_3$–C$_6$cycloalkyl, cyclopropylmethyl which is unsubstituted or substituted by 1 to 2 fluorine or chlorine atoms, cyano-C$_1$–C$_2$alkyl, phenyl-C$_1$–C$_2$alkyl which is unsubstituted or substituted by halogen, methyl, methoxy or halomethyl having 1 to 3 halogen atoms, it being possible for the phenyl group to be monosubstituted to disubstituted by identical or different substituents; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro; or R$_3$ and R$_4$ together with the nitrogen atom to which they are bonded are 1,2,4-triazolyl, 4-morpholinyl, 1-azepinyl, 1-piperidinyl or 1-pyrrolidinyl, R$_3$ is particularly preferably methyl;

(13) compounds of the formula I in which R$_4$ is methyl or phenyl, particularly methyl;

(14) compounds of the formula I in which

X is CH; Y is OCH$_3$; R$_1$ is CH$_3$; A is oxygen;

R$_2$ is either 4-methylphenyl or 4-allyloxyphenyl or 4-(3-trifluoromethyl-benzyloxy)phenyl or 4-(2,2-dichlorocyclopropylmethoxy)phenyl and R$_3$ is CH$_3$;

(15) compounds of the formula I in which either a) X is an N atom and

Y is OCH$_3$ or NHCH$_3$, or b) X is CH and
   Y is OCH$_3$,
and in which furthermore
   A is an O atom or the group NR$_4$;
   R$_1$ is hydrogen; C$_1$–C$_4$alkyl; cyclopropyl; cyano or methylthio;
   R$_2$ is hydrogen; C$_1$–C$_6$alkyl; C$_3$–C$_6$cycloalkyl; phenyl which is unsubstituted or monosubstituted to disubstituted, independently, by halogen, C$_1$–C$_4$alkyl, C$_1$–C$_4$alkoxy, C$_1$–C$_2$haloalkyl, C$_1$–C$_2$haloalkoxy, C$_3$–C$_6$alkenyloxy, C$_3$–C$_6$alkynyloxy, C$_1$–C$_4$alkylenedioxy, cyano or nitro; thienyl;
   R$_3$ is hydrogen; C$_1$–C$_6$alkyl; C$_1$–C$_6$haloalkyl having 1 to 5 halogen atoms; C$_1$–C$_4$alkoxy-C$_1$–C$_2$alkyl; C$_2$–C$_4$alkenyl-C$_1$–C$_2$alkyl which is unsubstituted or substituted by 1 to 3 halogen atoms; C$_2$–C$_4$alkynyl-C$_1$–C$_2$-alkyl; C$_3$–C$_6$cycloalkyl which is unsubstituted or substituted by 1 to 4 halogen atoms; C$_3$–C$_6$cycloalkyl-C$_1$–C$_4$alkyl which is unsubstituted or substituted by 1 to 4 halogen atoms; cyano-C$_1$–C$_4$alkyl; C$_1$–C$_4$alkoxycarbonyl-C$_1$–C$_2$alkyl; phenyl-C$_1$–C$_3$alkyl which is unsubstituted or substituted by halogen, C$_1$–C$_3$alkyl, C$_1$–C$_4$alkoxy, C$_1$–C$_4$haloalkyl, cyano, nitro, C$_1$–C$_4$alkylenedioxy, it being possible for the phenyl group to be monosubstituted to trisubstituted by identical or different substituents; phenyl which is unsubstituted or monosubstituted to disubstituted, independently, by C$_1$–C$_4$alkyl, C$_1$–C$_4$alkoxy, halogen, C$_1$–C$_2$haloalkyl having 1 to 3 halogen atoms, nitro or cyano; pyridyl which is unsubstituted or monosubstituted to disubstituted, independently, by C$_1$–C$_4$alkyl, C$_1$–C$_4$alkoxy, halogen, C$_1$–C$_2$haloalkyl having 1 to 3 halogen atoms, nitro or cyano;
   R$_4$ is C$_1$–C$_4$alkyl; phenyl; or
   R$_3$ and R$_4$ together with the nitrogen atom to which they are bonded form a saturated or unsaturated 5- to 7-membered ring which is unsubstituted or substituted by C$_1$–C$_4$alkyl and which can have 1 to 3 additional hetero atoms selected from amongst N, O and S.
(16) compounds of the formula I in which
   X is CH or N
   Y is OCH$_3$
   A is O or N—R$_4$
   R$_1$ is methyl, cyclopropyl or methylthio;
   R$_2$ is methyl; cyclopropyl; phenyl which is unsubstituted or monosubstituted to disubstituted, independently, by halogen, C$_1$–C$_4$alkyl, C$_1$–C$_4$alkoxy, C$_1$–C$_2$alkyl which is substituted by 1 to 5 halogen atoms, C$_1$–C$_2$haloalkoxy, C$_3$–C$_6$-alkenyloxy, C$_3$–C$_6$alkynyloxy, C$_1$–C$_4$alkylenedioxy, cyano, or nitro; or thienyl; and in which
   R$_3$ is as defined for formula I and
   R$_4$ is methyl or phenyl, or
   R$_3$ and R$_4$ together with the nitrogen atom to which they are bonded are either pyrrolidine, piperidine, morpholine, thiomorpholine, hexamethyleneimine, imidazole, pyrazole, pyrrole, 1,2,4-triazole or 1,2,3-triazole.
(17) Compounds of the formula I in which:
   X is N,
   Y is NHCH$_3$,
   A is O or N—R$_4$,
   R$_1$ is methyl, cyclopropyl or methylthio;
   R$_2$ is methyl; cyclopropyl; phenyl which is unsubstituted or monosubstituted to disubstituted, independently, by halogen, C$_1$–C$_4$alkyl, C$_1$–C$_4$alkoxy, C$_1$–C$_2$alkyl which is substituted by 1 to 5 halogen atoms, C$_1$–C$_2$haloalkoxy, C$_3$–C$_6$alkenyloxy, C$_3$–C$_6$alkynyloxy, C$_1$–C$_4$alkylenedioxy, cyano or nitro; or thienyl; and in which
   R$_3$ is as defined for formula I and
   R$_4$ is methyl or phenyl, or
   R$_3$ and R$_4$ together with the nitrogen atom to which they are bonded are either pyrrolidine, piperidine, morpholine, thiomorpholine, hexamethyleneimine, imidazole, pyrazole, pyrrole, 1,2,4-triazole or 1,2,3-triazole.
(18) Compounds of the formula I in which:
   A is oxygen,
   R$_1$ is methyl,
   R$_2$ is methyl; phenyl which is unsubstituted or monosubstituted to disubstituted, independently, by halogen, C$_1$–C$_4$alkyl C$_1$–C$_4$alkoxy, C$_1$–C$_2$alkyl which is substituted by 1 to 5 halogen atoms, C$_1$–C$_2$haloalkoxy, C$_3$–C$_6$alkenyloxy, C$_3$–C$_6$alkynyloxy, C$_1$–C$_4$alkylenedioxy, cyano or nitro; or thienyl; and
   R$_3$ is C$_1$–C$_6$alkyl;
while X and Y are as defined for formula I.
(19) Compounds of the formula I in which
   R$_1$ is methyl,
   R$_2$ is methyl and
   R$_3$ is as described and
   R$_4$ is methyl or phenyl, or
   R$_3$ and R$_4$ together with the nitrogen atom to which they are bonded form a saturated or unsaturated 5- to 7-membered ring which is unsubstituted or substituted by C$_1$–C$_4$alkyl and which can have 1 to 3 additional hetero atoms selected from amongst N, O and S;
while A, X and Y are as defined for formula I.
(20) Compounds of the formula I in which:
   R$_3$ is hydrogen; C$_1$–C$_4$alkyl; C$_1$–C$_4$haloalyl having 1 to 3 halogen atoms; C$_1$–C$_2$alkoxy-C$_1$–C$_2$alkyl; propenyl which is unsubstituted or substituted by 1 to 3 halogen atoms; propargyl; C$_3$–C$_6$cycloalkyl; C$_3$–C$_6$cycloalkylmethyl which is unsubstituted or substituted by 1 to 2 halogen atoms; cyano-C$_1$–C$_2$-alkyl, C$_1$–C$_2$alkoxycarbonyl-C$_1$–C$_2$alky; phenyl-C$_1$–C$_2$alkyl which is unsubstituted or substituted by halogen, methyl, methoxy, halomethyl having 1 to 3 halogen atoms, cyano, nitro or C$_1$–C$_2$alkylenedioxy, it being possible for the phenyl group to be monosubstituted to disubstituted by identical or different substituents; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro;
   R$_4$ is methyl or phenyl; or
   R$_3$ and R$_4$ together with the nitrogen atom to which they are bonded form a saturated or unsaturated 5- to 7-membered ring which is unsubstituted or substituted by C$_1$–C$_4$alkyl and which can have 1 to 3 additional hetero atoms selected from amongst N, O and S; while A, X, Y, R$_1$ and R$_2$ are as defined for formula I.
(21) Amongst the compounds of the formula I mentioned under (20), those in which R$_3$ and R$_4$ together with the nitrogen atom to which they are bonded are triazolyl, morpholinyl, 2,6-dimethylmorpholinyl, azepinyl, piperidyl or pyrrolidinyl.

(22) Compounds of the formula I in which:
A is oxygen,
$R_1$ is methyl,
$R_2$ is methyl; phenyl which is unsubstituted or monosubstituted to disubstituted, independently, by halogen, $C_1$–$C_4$alkyl, $C_1$–$C_4$alkoxy, $C_1$–$C_2$alkyl which is substituted by 1 to 5 halogen atoms, $C_1$–$C_2$haloalkoxy, $C_3$–$C_6$alkenyloxy, $C_3$–$C_6$alkynyloxy, $C_1$–$C_4$alkylenedioxy, cyano or nitro; or thienyl; and
$R_3$ is hydrogen; $C_1$–$C_4$alkyl; $C_1$–$C_4$haloalkyl having 1 to 3 halogen atoms; $C_1$–$C_2$alkoxy-$C_1$–$C_2$alkyl; propenyl which is unsubstituted or substituted by 1 to 3 halogen atoms; propargyl; $C_3$–$C_6$cycloalkyl; $C_3$–$C_6$cycloalkylmethyl which is unsubstituted or substituted by 1 to 2 halogen atoms; cyano-$C_1$–$C_2$-alkyl; $C_1$–$C_2$alkoxycarbonyl-$C_1$–$C_2$alkyl; phenyl-$C_1$–$C_2$alkyl which is unsubstituted or substituted by halogen, methyl, methoxy, halomethyl having 1 to 3 halogen atoms, cyano, nitro or $C_1$–$C_2$alkylenedioxy, it being possible for the phenyl group to be monosubstituted to disubstituted by identical or different substituents; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro; while X and Y are as defined for formula I.

(23) Amongst the compounds of the formula I mentioned under (22), those in which:
A is oxygen,
$R_1$ is methyl,
$R_2$ is methyl; phenyl which is unsubstituted or monosubstituted to disubstituted, independently, by halogen, methyl, methoxy, trifluoromethyl or trifluoromethoxy; and
$R_3$ is methyl.

(24) Compounds of the formula I in which:
A is $NCH_3$,
$R_1$ is methyl,
$R_2$ is methyl; phenyl which is unsubstituted or monosubstituted to disubstituted, independently, by halogen, methyl, methoxy, trifluoromethyl or trifluoromethoxy;
$R_3$ is methyl; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro;
while X and Y are as defined for formula I.

(25) Compounds of the formula I in which:
X is an N atom;
Y is $OR_{11}$;
$R_{11}$ is $C_1$–$C_4$alkyl; and in which
A, $R_1$, $R_2$ and $R_3$ are as defined for formula I.

(26) Amongst the compounds mentioned under (25), those in which:
A is an O atom;
$R_1$ and $R_2$ are methyl;
$R_3$ is hydrogen; $C_1$–$C_4$alkyl; $C_1$–$C_4$haloalkyl having 1 to 3 halogen atoms; $C_1$–$C_2$alkoxy-$C_1$–$C_2$alkyl; propenyl which is unsubstituted or substituted by 1 to 3 halogen atoms; propargyl; $C_3$–$C_6$cycloalkyl; $C_3$–$C_6$cycloalkylmethyl which is unsubstituted or substituted by 1 to 2 halogen atoms; cyano-$C_1$–$C_2$-alkyl; $C_1$–$C_2$alkoxycarbonyl-$C_1$–$C_2$alkyl; phenyl-$C_1$–$C_2$alkyl which is unsubstituted or substituted by halogen, methyl, methoxy, halomethyl having 1 to 3 halogen atoms, cyano, nitro or $C_1$–$C_2$alkylenedioxy, it being possible for the phenyl group to be monosubstituted to disubstituted by identical or different substituents; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro.

(27) Amongst the compounds mentioned under (26), those in which:
$R_3$ is hydrogen; $C_1$–$C_4$alkyl or $C_1$–$C_4$haloalkyl having 1 to 3 halogen atoms.

(28) Compounds of the formula I in which:
X is an N atom;
Y is $N(R_{12})R_{13}$;
$R_{12}$ and $R_{13}$, independently, are hydrogen or $C_1$–$C_4$alkyl; and in which
A, $R_1$, $R_2$ and $R_3$ are as defined for formula I.

(29) Amongst the compounds mentioned under (28), those in which:
Y is $NH_2$, $N(CH_3)_2$ or $NHC_2H_5$;
A is an O atom;
$R_1$ and $R_2$ are methyl;
$R_3$ is hydrogen; $C_1$–$C_4$alkyl; $C_1$–$C_4$haloalkyl having 1 to 3 halogen atoms; $C_1$–$C_2$alkoxy-$C_1$–$C_2$alkyl; propenyl which is unsubstituted or substituted by 1 to 3 halogen atoms; propargyl; $C_3$–$C_6$cycloalkyl; $C_3$–$C_6$cycloalkylmethyl which is unsubstituted or substituted by 1 to 2 halogen atoms; cyano-$C_1$–$C_2$-alkyl; $C_1$–$C_2$alkoxycarbonyl-$C_1$–$C_2$alkyl; phenyl-$C_1$–$C_2$alkyl which is unsubstituted or substituted by halogen, methyl, methoxy, halomethyl having 1 to 3 halogen atoms, cyano, nitro or $C_1$–$C_2$alkylenedioxy, it being possible for the phenyl group to be monosubstituted to disubstituted by identical or different substituents; phenyl which is unsubstituted or monosubstituted to disubstituted, independently, by halogen, methyl, methoxy, halomethyl having 1 to 3 halogen atoms, cyano or nitro; or pyridyl which is unsubstituted or monosubstituted to disubstituted, independently, by halogen, methyl, methoxy, halomethyl having 1 to 3 halogen atoms, cyano or nitro.

(30) Amongst the compounds mentioned under (29), those in which:
$R_3$ is hydrogen; $C_1$–$C_4$alkyl or $C_1$–$C_4$haloalkyl having 1 to 3 halogen atoms.

(31) Compounds of the formula I in which the X═C double bond is in the E form.

The compounds of the formula I can be prepared as follows:

A) To obtain a compound of the formula I in which Y is $N(R_{12})R_{13}$, a compound of the formula I in which Y is $OR_{11}$ is reacted with $HN(R_{12})R_{13}$. The reaction is carried out advantageously in an inert organic diluent, for example in an alcohol such as ethanol, in an ether such as tetrahydrofuran or dioxane, an ester such as ethyl acetate, a sulfoxide such as dimethyl sulfoxide, an amide such as dimethylformamide or a ketone such as methyl isobutyl ketone. Methylamine can be used in gaseous form or else in dissolved form, for example in the form of a solution in ethanol. The process temperature is conventionally between 0° C. and 40° C., preferably room temperature.

B) To prepare a compound of the formula I in which X, Y, A and $R_1$–$R_3$ are as defined for formula I (and in which $R_3$ is not hydrogen), A compound of the general formula

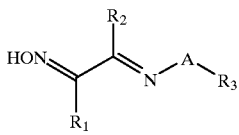

II in which A and $R_1$–$R_3$ are as defined above is reacted with a compound of the general formula

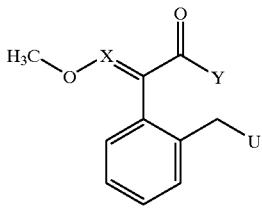

III in which X and Y are as defined above and U is a leaving group.

This reaction is a nucleophilic substitution reaction which can be carried out under the reaction conditions conventionally used in such a case. The leaving group U is preferably chlorine, bromine, iodine, mesyloxy or tosyloxy. The reaction is advantageously carried about in an inert organic diluent such as a cyclic ether, for example tetrahydrofuran or dioxane, a ketone such as acetone, an amide such as dimethylformamide, a sulfoxide such as dimethyl sulfoxide, in the presence of a base such as sodium hydride, sodium carbonate, potassium carbonate, sodium amide, a tertiary amine, for example trialkylamine, in particular diazabicyclononane or diazabicycloundecane, or silver oxide, at temperatures between –20° C. and 80° C., preferably in a temperature range of 0° C. to 50° C.

Alternatively, the reaction can be carried out with phase transfer catalysis in an organic solvent for example methylene chloride, in the presence of an aqueous alkaline solution, for example sodium hydroxide solution, and of a phase transfer catalyst, for example tetrabutylammonium hydrogen sulfate, at room temperature.

The resulting compounds of the formula I can be isolated and purified by methods known per se. Equally, isomer mixtures obtained, for example E/Z isomer mixtures, can be separated by methods known per se to give the pure isomers, for example by means of chromatography or fractional crystallization.

The oximes of the general formula II which are used as starting materials are either known or can be prepared by known methods (J. Chem. Soc., Perkin Trans II 537 (1990); Ber. Deutsch. Chem. Ges. 62, 866 (1929); Gazz. Chim. Ital. 37 II, 147 (1907); Liebigs Ann. Chem. 262, 305 (1891)).

Equally, the starting materials of the formula III can be prepared in a manner known per se, for example as described in, the European Patent Publication EP-A-203 606 (BASF) and the literature cited therein, or as described in Angew. Chem. 71, 349–365 (1959).

C) To prepare a compound of the formula I in which A is oxygen and X, Y and $R_1$–$R_3$ are as defined for formula I:

A compound of the general formula

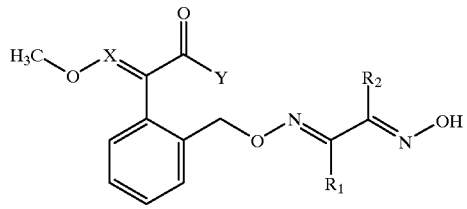

IV in which X, Y, $R_1$ and $R_2$ are as defined above is reacted with a compound of the general formula

V, $R_3$ being as defined under formula I and U being as defined under formula III (and $R_3$ being neither hydrogen nor phenyl nor pyridyl).

This reaction is a nucleophilic substitution reaction as described under B).

D) To prepare a compound of the formula IV in which X, Y, $R_1$ and $R_2$ are as defined for formula I, a procedure is followed in which:

A compound of the general formula

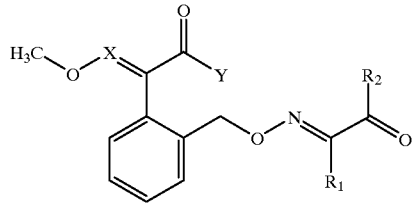

VI in which X, Y, $R_1$ and $R_2$ are as defined above is reacted with hydroxylamine or a salt thereof, for example the hydrochloride. The reaction is carried out advantageously in pyridine or methanol as the solvent at temperatures between –20° C. and +80° C. or the boiling point of methanol, preferably in a temperature range of 0° C. to 50° C., a base being required if methanol is used, for example an alkali metal carbonate, such as potassium carbonate, a tertiary amine such as triethylamine or diazabicyclononane, pyridine or silver oxide.

The ketone of the general formula VI is prepared analogously to the method described under B). The ketones of the general formula VI and their preparation are described, for example, in EP-370 629, EP-506 149, EP403 618, EP414 153, EP-463 488, EP472 300, EP-460 575, WO-92/18494 and in other publications.

E) To prepare a compound of the formula I in which A, X, Y and $R_1$–$R_3$ are as defined for formula I but in which $R_3$ is not hydrogen, a procedure is followed in which, for example:

A compound of the general formula

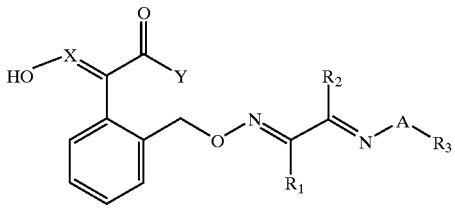

VII in which A, X, Y and R$_1$–R$_3$ are as defined above is reacted with a methylating agent, for example methyl iodide, dimethyl sulfate or diazomethane. The reaction is advantageously carried out in the presence of a base, for example potassium carbonate or sodium hydride, in a suitable solvent and at suitable reaction temperatures (see, for example, H. S. Anker und H. T. Clarke; Organic Synthesis, Coll. Vol. 3, 172).

F) To prepare a compound of the formula VII in which A, X, Y and R$_1$–R$_3$ are as defined for formula I, a procedure is advantageously followed in which:

A compound of the formula

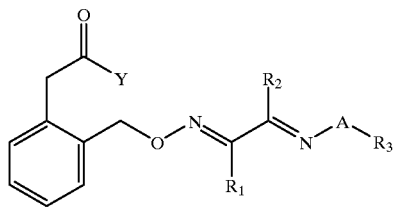

VIII in which A, Y and R$_1$–R$_3$ are as defined above is reacted with a formate in the presence of a base analogously to the method described in EP-A-178 826, or is subjected to nitrosation with nitrous acid or a nitrite in the presence of a base analogously to the method described in EP-A-254 426.

A further possibility of synthesizing a compound of the formula VII is the following reaction:

A compound of the formula

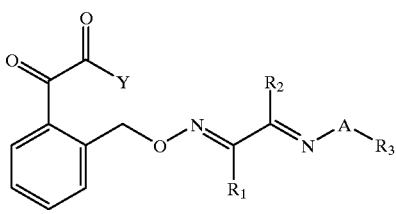

IX in which A, Y and R$_1$ to R$_3$ are as defined above is reacted with methoxymethylenetriphenylphosphorane analogously to the method described in EP-A-178 826 or with O-methylhydroxylamine (or a salt thereof) analogously to the method described in EP-A-254 426.

The novel compounds of the formulae II, VII, VIII and IX are also provided by the invention. Preferred thereof are the following compounds:

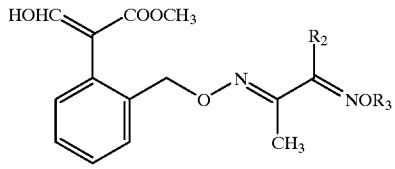

VII.1

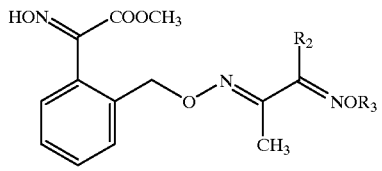

VII.2

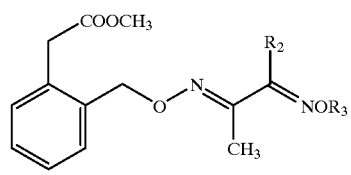

VIII.1

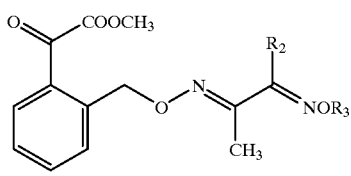

IX.1 in which R$_2$ and R$_3$ are as defined for formula I; and the compounds

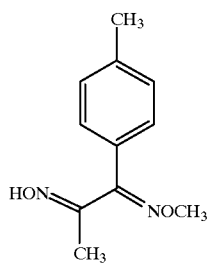

II.1

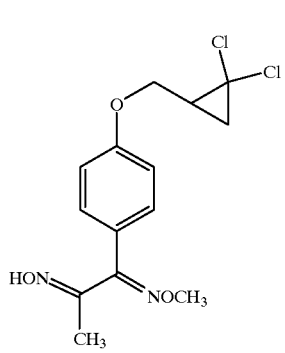

II.2

It has now been found that compounds of the formula I have a microbicidal spectrum for controlling phytopathogenic microorganisms, in particular fungi, which is particularly favourable for practical requirements. They have very advantageous curative, preventive and, in particular, systemic properties and can be used for protecting a large number of crop plants. Using the active ingredients of the formula I, the pests which are found on plants or parts of plants (fruits, flowers, foliage, stalks, tubers, roots) of various crops of useful plants can be contained or destroyed, and even parts of plants which are formed at a later point in time remain free from phytopathogenic microorganisms.

The compounds of the formula I can furthermore be used as seed-dressing agents for the treatment of seed (fruits, tubers, grains) and nursery plants for the protection against fungal infections and against soil-borne phytopathogenic fungi.

Compounds of the formula I are active for example against phytopathogenic fungi which belong to the following classes: Fungi imperfecti (in particular Botryts, furthermore Pyricularia, Helminthosporium, Fusarium, Septoria, Cercospora, Cercosporella and Alternaria); Basidiomycetes (for example Rhizoctonia, Hemileia, Puccinia); Ascomycetes (for example Venturia and Erysiphe, Podosphaera, Monninia, Uncinula); Oomycetes (for example Phytophthora, Peronospora, Bremia, Pythium, Plasmopara).

Compounds of the formula I are furthermore valuable active ingredients against insects and Acarina which are found on useful plants and ornamentals in agriculture and horticulture, in particular in crops of rice, cotton, vegetables and fruit, and in forests, and are well tolerated by warm-blooded species, fish and plants. The compounds I are particularly suitable for controlling insects in crops of rice, fruit and vegetables, in particular plant-injurious insects. Other fields of application for the active ingredients of the invention are the protection of stored products and materials and, in the hygiene sector, in particular the protection of domestic animals and productive livestock The compounds of the formula I are active against all or individual development stages of normally sensitive, but also resistant, pest species. Their activity can become apparent, for example, from the destruction of the pests, either immediately or only after some time has elapsed, for example during molting, or from reduced oviposition and/or hatching rates.

The abovementioned animal pests include, for example: from the order Lepidoptera, for example,
Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp, Sesamia spp., Sparganothis spp., Spodoptera spp., Synanthedon spp., Thaumetopoea spp., Tortrix spp., *Trichoplusia ni* and Yponomeuta spp.;
from the order Coleoptera, for example,
Agrotis spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;
from the order Orthoptera, for example,
Blatta spp., Blattella spp., Gryllotalpa spp., *Leucophaea maderae*, Locusta spp., Periplaneta spp. and Schistocerca spp.;
from the order Isoptera, for example,
Reticulitermes spp.;
from the order Psocoptera, for example,
Liposcelis spp.;
from the order Anoplura, for example,
Haematopinus spp., Linognathus spp., Pediculus spp., Pemphigus spp. and Phylloxera spp.;
from the order Mallophaga, for example,
Damalinea spp. and Trichodectes spp.;
from the order Thysanoptera, for example,
Frankliniella spp., Hercinothrips spp., Taeniotlirips spp., Thrips palmi, *Thrips tabaci* and *Scirtothrips aurantii*;
from the order Heteroptera, for example,
Cimex spp., *Distantiella theobroma*, Dysdercus spp., Euchistus spp. Eurygaster spp. Leptocorisa spp., Nezara spp., Piesma spp., Rhodnius spp., *Sahlbergella singularis*, Scotinophara spp. and Triatoma spp.;
from the order Homoptera, for example,
*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma langerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria Spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri*;
from the order Hymenoptera, for example,
Acromyrmex, Atta spp., Cephus spp., Diprion spp., Diprionidae, *Gilpinia polytoma*, Hoplocampa spp., Lasius spp., *Monomorium phamonis*, Neodiprion spp., Solenopsis spp. and Vespa spp.;
from the order Diptera, for example,
Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;
from the order Siphonaptera, for example,
Ceratophyllus spp. and *Xenopsylla cheopis*;
from the order Thysanura, for example,
*Lepisma saccharina* and
from the order Acarina, for example,
Acarus siro, *Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus galiinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.

Target crops for crop-protecting use are, within the scope of the invention, for example the following types of plants:

cereals (wheat, barley, rye, oats, rice, maize, sorghum and related species); beet (sugar and fodder beet); pome fruit, stone fruit and soft fruit (apples, pears, plums, peaches, almonds, cherries, strawberries, raspberries and blackberries); pulses (beans, lentils, peas, soya beans); oil crops (oilseed rape, mustard, poppy, olives, sunflowers, coconut, castor, cocoa, groundnuts); cucurbits (pumpkin, cucumbers, melons); fibre plants (cotton, flax, hemp, jute); citrus fruit (oranges, lemons, grapefruit, tangerines); vegetables (spinach, lettuce, asparagus, cabbages, carrots, onions, tomatoes, potatoes, bell pepper); the laurel family (avocado, cinnammon, camphor), and plants such as tobacco, nuts, coffee, egg plants, sugarcane, tea, pepper, vines, hops, the banana family, latex plants and ornamentals.

The action of the compounds of the formula I according to the invention and of the compositions comprising them can be broadened considerably and adapted to prevailing circumstances by adding other microbicides, insecticides and/or acaricides. Representatives of the following active ingredient classes are examples of suitable additives: organophosphorus compounds, nitrophenols and derivatives, formamidines, ureas, carbamates, pyrethroids, chlorinated hydrocarbons and Bacillus thuringiensis preparations.

As a rule, active ingredients of the formula I are used in the form of compositions and can be applied to the area or plants to be treated simultaneously or in succession with other active ingredients. These other active ingredients can be fertilizers, trace element mediators or other preparations which have an effect on plant growth. Selective herbicides and also insecticides, fungicides, bactericides, nematicides, mofluscicides or mixtures of a plurality of these preparations, with or without other carriers conventionally used in the art of formulation, surfactants or other application-enhancing additives, can also be used.

Suitable carriers and additives can be solid or liquid and are those substances which are expedient in the art of formulation, for example natural or regenerated mineral substances, solvents, dispersants, wetting agents, tackifiers, thickeners, binders or fertilizers.

The following are suitable solvents: aromatic hydrocarbons, preferably the fractions $C_8$ to $C_{12}$, for example xylene mixtures or substituted naphthalenes, phthalates such as dibutyl phthalate or dioctyl phthalate, aliphatic hydrocarbons such as cyclohexane or paraffins, alcohols and glycols as well as their ethers and esters, such as ethanol, ethylene glycol, ethylene glycol monomethyl ether or ethyl ether, ketones such as cyclohexanone, strongly polar solvents, such as N-methyl-2-pyrrolidone, dimethyl sulfoxide or dimethylformamide, and unepoxidized or epoxidized vegetable oils, such as epoxidized coconut oil or soya oil; or water.

Solid carriers which are generally used, for example for dusts and dispersible powders, are ground natural rocks, such as calcite, talc, kaolin, montmorillonite or attapulgite.

Particularly advantageous application enhancing additives which may result in a greatly reduced rate of application are, moreover, natural (animal or vegetable) or synthetic phospholipids from the series of the cephalins and lecithins, which can be obtained from, for example, soya beans.

Suitable surface-active compounds are, depending on the nature of the active ingredient of the formula I to be formulated, non-ionic, cationic and/or anionic surfactants which have good emulsify, dispersing and wetting properties. Surfactants are also to be understood as meaning surfactant mixtures.

Suitable anionic surfactants can be so-called water-soluble salts and also watersoluble synthetic surface-active compounds.

Soaps are the alkali metal salts, alkaline earth metal salts or substituted or unsubstituted ammonium salts of higher fatty acids ($C_{10}$–$C_{22}$), for example the sodium salts or potassium salts of oleic or stearic acid, or of natural mixtures of fatty acids which can be obtained from, for example, coconut oil or tallow oil. The fatty acid methyltaurates must also be mentioned.

Suitable non-ionic surfactants are polyglycol ether derivatives of aliphatic or cycloaliphatic alcohols, saturated or unsaturated fatty acids and alkylphenols which have 3 to 30 glycol ether groups and 8 to 20 carbon atoms in the (aliphatic) hydrocarbon radical and 6 to 18 carbon atoms in the alkyl radical of the alkylphenols.

Examples of non-ionic surfactans are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Other suitable substances are fatty acid esters of polyoxyethylene sorbitan, such as polyoxyethylene sorbitan trioleate.

The cationic surfactants are mainly quaternary ammonium salts which have, as N-substituents, at least one alkyl radical having 8 to 22 C atoms and, as further substituents, lower, halogenated or free alkyl, benzyl or lower hydroxyalkyl radicals.

As a rule, the agrochemical preparations comprise 0.1 to 99%, in particular 0.1 to 95%, of active ingredient of the formula I, 99.9 to 1%, in particular 99.9 to 5%, of a solid or liquid additive and 0 to 25%, in particular 0.1 to 25%, of a surfactant While concentrated compositions are more preferred as commercial products, the end consumer will, as a rule, use dilute compositions.

The compositions can also comprise other additives such as stabilizers, antifoams, viscosity regulators, binders, tackifiers, fertilizers or other active ingredients for achieving specific effects.

The formulations, i.e. the compositions, preparations or combinations comprising the active ingredient of the formula I together or without a solid or liquid additive, are produced in a known manner, for example by intimately mixing and/or grinding the active ingredient with an extender, for example a solvent (mixture), a solid carrier and, if appropriate, surface-active compounds (surfactants).

A preferred process for applying an active ingredient of the formula I or an agrochemical composition which comprises at least one of these active ingredients, is application to the foliage (foliar application). Frequency and rate of application depend on the danger of attack by the pathogen in question. However, the active ingredients of the formula I can also reach the plant via the soil through the root system (systemic action) by drenching the locus of the plant with a liquid preparation or by incorporating the substances in solid form into the soil, for example in the form of granules (soil application). In the case of paddy rice, such granules can be metered out into the flooded rice field. Alternatively, the compounds of the formula I can be applied to seed kernels (coating), either by soaking the kernels in a liquid preparation of the active ingredient or by coating them with a solid preparation. In principle, any type of plant propagation material can be protected using the compounds of the formula I, for example seed, roots or stalks.

The compounds of the formula I are used as pure compounds or, preferably, together with the auxiliaries conventionally used in the art of formulation. To this end, they are advantageously processed in the known manner, for example to give emulsion concentrates, spreadable pastes, directly sprayable or dilutable solutions, dilute emulsions, wettable powders, soluble powders, dusts, granules, and encapsulations, for example in polymeric substances. The methods of application, such as spraying, atomizing, dusting, broadcasting, painting on or pouring, as well as the nature of the compositions are selected to suit the intended aims and the prevailing circumstances. Favourable rates of application are, as a rule, 1 g to 2 kg of active ingredient (a.i.) per ha, preferably 25 g to 800 g of a.i./ha, particularly preferably 50 g to 400 g of a.i./ha. When used as seed dessing products, dosage rates of 0.001 g to 1.0 g of active ingredient are advantageously used per kg of seed.

The examples which follow are intended to illustrate the invention in greater detail without imposing any restriction thereto.

PREPARATION EXAMPLES

Example H-1

Preparation of

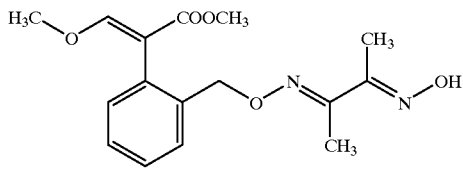

1.32 g of hydroxylamine hydrochloride are added to a solution of 5.2 g of methyl 3-Methoxy-2-[([(3-oxo-2-butyl)iminoloxy]o-tolyl]acrylate (EP-A-370 629, No. 156) in 20 ml of pyridine. After the mixture has been stirred for 6 hours at 30° C., ice-water is added, the crystal cake which has formed after a few hours is filtered off, and the crystals are washed with water. Recrystallization from ethanol/water gives 4.8 g of methyl 3-methoxy-2-[([(3-hydroximino-2-butyl)imino]oxy)o-tolyl]acrylate (Comp. No. 1.73) as yellow crystals of melting point 104–107° C.

Example H-2

Preparation of

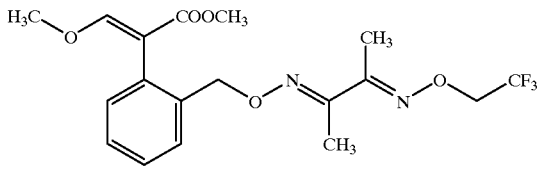

In a pressure pipe, 5 ml of dimethylformamide are added to 0.2 g of an approximately 65% sodium hydride suspension washed with hexane. Then, 1.6 g of methyl 3-methoxy-2-[([(3-hydroximino-2-butyl)imino]oxy)o-tolyl]acrylate and hereupon 1.1 g of 2,2,2-trifluoroethyl iodide are added. After the evolution of hydrogen has subsided, the pressure pipe is sealed, and the mixture is stirred for 5 hours at 50° C. Then, the reaction solution is poured into ice-water and extracted using ethyl acetate, and the product is chromatographed on silica gel using ethyl acetate/hexane (1:3). This gives 1.2 g of methyl 3-methoxy-2-[([(3-(2,2,2-trifluoroethoxyimino)-2-butyl)imino]oxy)o-tolyl]acrylate (Comp. No. 1.74) as a colourless oil. $^1$H NMR in CDCl$_3$: chemical shift of the two imino-substituted methyl groups: 1.99 and 2.04 ppm.

Example H-3

Preparation of

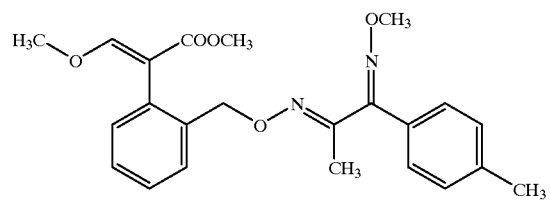

A solution of 15.0 g of p-methylpropiophenone and 20 ml of isopentyl nitrite in 30 ml of methanol is slowly added dropwise to 20 ml of sodium methylate (30% in methanol). After the mixture has been stirred for 5 hours, 30 ml of water are added dropwise, and the mixture is subsequently acidified using acetic acid. The mixture is extracted using ethyl acetate, and the extract is washed with water, dried (Na$_2$SO$_4$) and concentrated in vacuo. The residue is recrystallized from diethyl etherin-hexane. This gives α-hydroxyimino-4methylpropiophenone as colourless crystals of melting point 122–124° C.

8.1 g of the previously obtained compound and 4.6 g of o-methylhydroxylamine hydrochloride in 40 ml of pyridine are refluxed for 1 hour. After an addition of toluene, the mixture is concentrated in vacuo, treated with water and extracted using ethyl acetate. The organic phase is washed with water, dried over sodium sulfate and concentrated in vacuo. α-Hydroxyimino-4-methylpropiophenone O-methyl oxime are crystallized from diethyl ether/n-hexane in the form of colourless crystals of melting point 156–157° C.

1.87 g of the previously obtained oxime and 2.58 g of methyl 2-(α-bromo-o-tolyl)-3-methoxyacrylate are added to a suspension of 0.41 g of sodium hydride in 25 ml of N,N-dimethylformamide, and the reaction mixture is stirred for 3 hours. It is then acidified using acetic acid, treated with water and extracted using ethyl acetate. The organic phase is washed twice using saturated sodium hydrogen carbonate solution and once using saturated sodium chloride solution. After drying over anhydrous sodium sulfate, the solvent is distilled off in vacuo. H-3 crystallizes from diethyl ether/n-hexane in the form of colorless crystals of melting point 98–101° C. (Comp. No. 1.117).

Example H-4

Preparation of

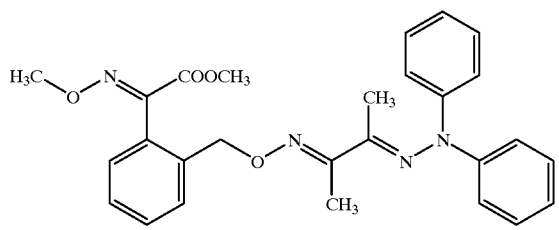

0.37 g of an approximately 65% sodium hydride suspension is washed with hexane, and 10 ml of dimethylformamide are added. A mixture of 2.59 g of methyl 2-(2-bromomethylphenyl)glyoxylate O-methyloxime and 2.42 g of 2-(diphenylhydrazono)-3-hydroximinobutane is added to this suspension, and the mixture is subsequently heated to 40–50° C. using a hot-air blower until hydrogen is evolved vigorously. The mixture is then stirred for one hour with the exclusion of moisture, and poured into ice-water. Extraction using ethyl acetate and chromatography on silica gel using ethyl acetate/hexane (1:2) gives 3.7 g of methyl 2-[([(3-diphenylhydrazono-2-butyl)-iminoloxy)o-tolyl]glyoxylate O-methyloxime (Comp. No. 2.19) as a yellow oil.

¹H NMR in CDCl₃: chemical shift of the two imino-substituted methyl groups: 1.64 and 2.12 ppm.

Example H-5

Preparation of

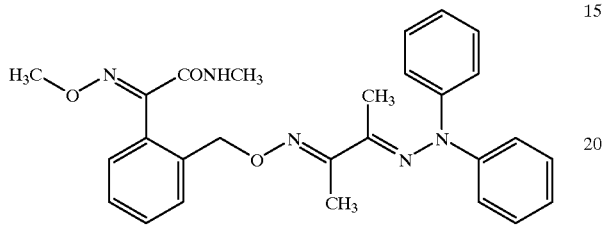

1.9 g of methyl 2-[({(3-diphenylhydrazono-2-butyl)imino}oxy)o-tolyl]glyoxylate O-methyloxime are stirred for 2 hours at room temperature in 10 ml of a 33% methylamine solution in ethanol Ethanol and the excess of methylamine are distilled off. The residue is taken up in diethyl ether, the solution is filtered, the filtrate is evaporated to dryness, the product remaining as a crystalline solid. Washing with hexane gives 1.8 g of N-monomethyl 2-({(3-diphenylhydrazono-2-butyl)imino}oxy)o-tolyl] glyoxylamide O-methyloxime (Comp. No. 3.19) as pale beige crystals of melting point 135–136° C.

Example H-6

Preparation of

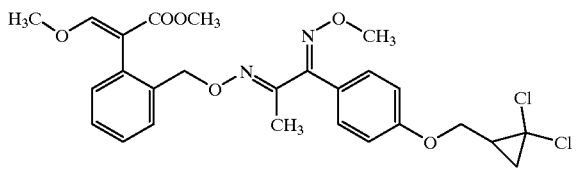

1.74 g of 1-[4(2,2-dichlorocyclopropylmethoxy)phenyl] propane-1,2-dione 1-(O-methyloxime)-2-oxime, of the formula (AA), are added to 0.13 g of sodium hydride in 25 ml of NN-dimethylformamide. 1.5 g of methyl 2-(2-bromomethylphenyl)-3-methoxyacrylate, of the formula (BB), are subsequently added, and the mixture is stirred for 3 hours at room temperature. The mixture is acidified using acetic acid, and water and ethyl acetate are added. The aqueous phase is separated off, and the organic phase is washed once using saturated sodium hydrogen carbonate solution and dried over anhydrous sodium sulfate. The solvent is evaporated in vacuo, and the residue obtained is purified on silica gel using hexane/ethyl acetate (3:1). The title compound is obtained as an oil. Separation by column chromatography on silica gel (hexane:ethyl acetate solution 3:1) gives three isomers: isomer A, m.p. 86–88° C., isomer B, oil, isomer C, oil (Compound 5.9).

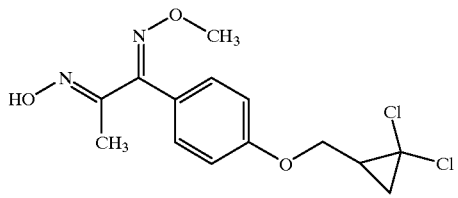

(AA)

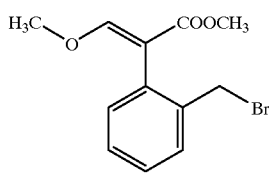

(BB)

Example H-7 (Intermediate)

Preparation of

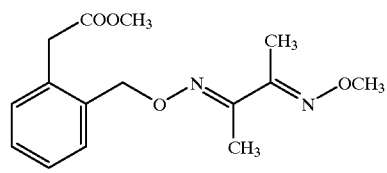

0.24 g of a c. 60% sodium hydride suspension is washed with hexane, and 10 ml of dimethyl formamide are added. To this suspension is then added a mixture of 2.4 g of 2-methyl bromomethylphenyl acetate and 1.3 g of diacetyl-dioxime monomethyl ether in 5 ml of dimethyl formamide and the mixture is then heated with a hot air blower to 40 to 50° C. until vigorous evolution of hydrogen occurs. This mixture is then stirred for 0.5 h under anhydrous conditions and poured onto ice/water. Extraction with ethyl acetate and chromatography with ethyl acetate/hexane (1:4) over silica gel give 1.4 g of the above compound in the form of a colourless oil.

¹H-NMR in CDCl₃: δ ppm: 1.98 (s,3H); 2.01 (s,3H); 3.68 (s,3H); 3.79 (s,2H); 3.94 (s,3H); 5.22 (s,2H); 7.18–7.42 (m,4H).

Example H-8 (Intermediate)

Preparation of

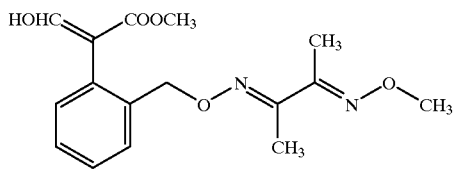

A solution of 18.74 g of the compound of Example P-7, 15.0 g of methyl formate and 0.2 g of methanol in 70 ml of tert-butylmethyl ether are added dropwise at room temperature over 2 h to a suspension of 2.99 g of sodium hydride in 45 ml of tert-butylmethyl ether. This mixture is stirred overnight and, after addition of 2 ml of methanol, poured onto ice/water. The pH is adjusted to 5 with 10 ml of acetic acid and extraction is carried out with ethyl acetate. The organic phase is dried over sodium sulfate and the solvent is removed by evaporation, giving 19.6 g of the compound in the form of a yellow oil.

$^1$H-NMR in CDCl$_3$: δ ppm: 1.98 (s,3H); 2.02 (s,3H); 3.73 (s,3H); 3.94 (s,3H); 5.11 (s,2H); 7.15–7.51 (m,5H); 12.00 (d,1H);

Example H-9 (Intermediate)

Preparation of

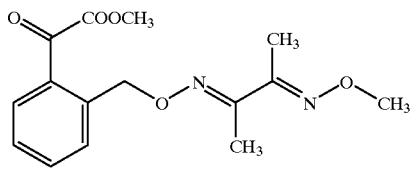

2.9 g of a c. 60% sodium hydride suspension are washed with hexane, and 50 ml of dimethyl formamide are added. To this suspension is then added a mixture of 14.3 g of methyl α-bromo-o-tolylglyoxylate and 7.2 g of 2-hydroximino-3-methoximinobutane in 20 ml of dimethyl formamide and the mixture is stirred for 3 h at room temperature under anhydrous conditions. This mixture is then poured onto ice/water and extracted with ethyl acetate. The organic phase is dried over sodium sulfate and concentrated on a rotary evaporator. The residue is crystallised from diethyl ether/hexane, to give the product in the form of beige crystals, m.p. 81–83° C.

Example H-10 (Intermediate)

Preparation of

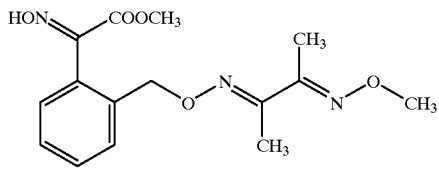

10 ml of pyridine and 0.41 g of hydroxylamime hydrochloride are added to 1.5 g of the compound of Example P-9. The mixture is stained for 4 h at room temperature, poured onto ice/water and extracted with ethyl acetate. The organic phase is dried over sodium sulfate and concentrated on a rotary evaporator. The residue is crystallised from diethyl ether/hexane, to give the product in the form of beige crystals, m.p. 78–81° C.

The following compounds can be prepared in this manner or analogously to one of the methods described further above:

(Abbreviations: Me=methyl, Et=ethyl, Δ=cyclopropyl, Ph=phenyl, m.p.=melting point).

NMR: The chemical shifts are given as δ (ppm) in CDCl$_3$.

TABLE 1

| Ex. No. | A | R$_1$ | R$_2$ | R$_3$ or NR$_3$R$_4$ | Physical data** |
|---|---|---|---|---|---|
| 1.1 | NMe | Me | Me | 6-CF$_3$-2-pyridyl | 2.17/2.19 |
| 1.2 | NMe | H | Me | 6-CF$_3$-2-pyridyl | |
| 1.3 | NMe | Me | Δ | 6-CF$_3$-2-pyridyl | |
| 1.4 | NMe | Me | H | phenyl | |
| 1.5 | NMe | Me | Me | phenyl | 2.09/2.18 |
| 1.6 | NMe | Δ | Me | phenyl | |
| 1.7 | NMe | Me | Me | 4-CF$_3$-2-pyridyl | m.p. 100° C. |
| 1.8 | NMe | H | Me | 4-CF$_3$-2-pyridyl | |
| 1.9 | NMe | Δ | Δ | phenyl | |
| 1.10 | NMe | Me | Me | 5-CF$_3$-2-pyridyl | 2.17/2.18 |
| 1.11 | NMe | H | Me | 5-CF$_3$-2-pyridyl | |
| 1.12 | — | H | Me | 4-(1,2,4-triazolyl) | |
| 1.13 | — | Me | Me | 4-(1,2,4-triazolyl) | 161–163° C. |
| 1.14 | — | Me | Δ | 4-(1,2,4-triazolyl) | |
| 1.15 | — | Me | Δ | 4-morpholinyl | |
| 1.16 | — | Me | Me | 4-morpholinyl | 113° C. |
| 1.17 | — | H | Me | 4-morpholinyl | |
| 1.18 | NPh* | H | Me | phenyl | |
| 1.19 | NPh* | Me | Me | phenyl | 1.74/2.22 |
| 1.20 | NPh* | Me | Δ | phenyl | |
| 1.21 | NPh* | Δ | Me | phenyl | |
| 1.22 | NMe | Me | Me | 2-nitrophenyl | 1.93/2.06 |
| 1.23 | NMe | H | Me | 2-nitrophenyl | |
| 1.24 | O | Me | Me | Me | 76–78° C. |
| 1.25 | O | H | Me | Me | 1.97/7.68 |
| 1.26 | O | Δ | Me | Me | 1.96/2.00 |
| 1.27 | O | Me | Δ | Me | 60–62° C. |
| 1.28 | O | Me | H | Me | |
| 1.29 | NMe | H | Me | 3-CF$_3$-2-pyridyl | |
| 1.30 | NMe | Me | Me | 3-CF$_3$-2-pyridyl | 2.06/2.18 |
| 1.31 | NMe | Δ | Me | 3-CF$_3$-2-pyridyl | |
| 1.32 | NMe | Δ | Me | 3-nitro-2-pyridyl | |
| 1.33 | NMe | H | Me | 3-nitro-2-pyridyl | |
| 1.34 | NMe | Me | Me | 3-nitro-2-pyridyl | 1.94/2.26 |
| 1.35 | NMe | Me | Me | 2-CF$_3$-phenyl | 1.85/2.10 |
| 1.36 | NMe | Me | Δ | 2-CF$_3$-phenyl | |
| 1.37 | NMe | H | Me | 2-CF$_3$-phenyl | |
| 1.38 | NMe | Me | Me | 3-CF$_3$-phenyl | |
| 1.39 | NMe | Me | Δ | 3-CF$_3$-phenyl | |
| 1.40 | NMe | H | Me | 4-CF$_3$-phenyl | |
| 1.41 | NMe | Me | Me | 4-CF$_3$-phenyl | |
| 1.42 | NMe | Me | Me | 2-chlorophenyl | 1.73/2.13 |
| 1.43 | NMe | Me | Me | 3-chlorophenyl | 2.12/2.17 |
| 1.44 | NMe | H | Me | 4-chlorophenyl | |
| 1.45 | NMe | Me | Me | 4-chlorophenyl | 2.10/2.15 |
| 1.46 | O | Me | Me | phenyl | 2.14/2.22 |
| 1.47 | O | Me | Δ | phenyl | |
| 1.48 | O | Me | Me | benzyl | 106–108° C. |
| 1.49 | O | Me | Me | Et | 1.92/1.95 |
| 1.50 | O | H | Me | Et | |
| 1.51 | O | Δ | Me | Et | |
| 1.52 | O | Me | Δ | Et | |
| 1.53 | O | Me | H | Et | |
| 1.54 | O | H | Me | methoxymethyl | |
| 1.55 | O | Me | Me | methoxymethyl | 83–84° C. |
| 1.56 | O | Me | Δ | methoxymethyl | |
| 1.57 | O | Δ | Me | methoxymethyl | |
| 1.58 | O | Me | Me | ethoxymethyl | 2.04/2.04 |
| 1.59 | O | H | Me | cyanomethyl | |
| 1.60 | O | Me | Me | cyanomethyl | 2.04/2.04 |
| 1.61 | O | Δ | Me | cyanomethyl | |
| 1.62 | — | Me | Me | azepino | 2.02/2.04 |
| 1.63 | — | Me | Me | piperidino | |

TABLE 1-continued

[Structure: H₃C-O-CH=C(COOCH₃)-phenyl-CH₂-O-N=C(R₁)-C(R₂)=N-A-R₃]

| Ex. No. | A | R₁ | R₂ | R₃ or NR₃R₄ | Physical data** |
|---|---|---|---|---|---|
| 1.64 | — | Me | Me | pyrrolidino | |
| 1.65 | O | H | Me | tert-butyl | |
| 1.66 | O | Me | Me | tert-butyl | 1.96/2.04 |
| 1.67 | O | Me | Me | propargyl | 114–115° C. |
| 1.68 | O | Δ | Me | propargyl | |
| 1.69 | O | Me | Δ | propargyl | |
| 1.70 | O | Me | Me | 2,2-dichloro-cyclopropylmethyl | 2.02/2.02 |
| 1.71 | O | Δ | Me | 2,2-dichloro-cyclopropylmethyl | |
| 1.72 | O | H | Me | H | |
| 1.73 | O | Me | Me | H | 104–107° C. |
| 1.74 | O | Me | Me | CF₃CH₂ | 1.99/2.04 |
| 1.75 | O | Δ | Me | CF₃CH₂ | |
| 1.76 | O | Me | H | CF₃CH₂ | |
| 1.77 | O | Me | H | CF₃CH₂CH₂ | |
| 1.78 | O | Me | Me | CF₃CH₂CH₂ | |
| 1.79 | O | Me | Me | CF₃CH₂CH₂CH₂ | 2.10/2.13 |
| 1.80 | O | Δ | Me | CF₃CH₂CH₂CH₂ | |
| 1.81 | NMe | Me | Me | Me | 94–98° C. |
| 1.82 | NMe | Me | Δ | Me | |
| 1.83 | O | Me | Me | CH₂·—CCl=CH₂ | 80° C. |
| 1.84 | O | Δ | Me | CH₂·—CCl=CH₂ | |
| 1.85 | O | Me | Me | propyl | |
| 1.86 | O | Me | Me | butyl | 36–38° C. |
| 1.87 | O | Me | Me | hexyl | 1.99/2.01 |
| 1.88 | O | Me | Me | methoxycarbonyl-methyl | 90–93° C. |
| 1.89 | O | H | Me | methoxycarbonyl-methyl | |
| 1.90 | O | Me | Me | 3-fluorobenzyl | 2.00/2.04 |
| 1.91 | O | Me | Me | 4-chlorobenzyl | |
| 1.92 | O | Me | Me | 2-chlorobenzyl | |
| 1.93 | O | Me | Me | 2-CF₃-benzyl | |
| 1.94 | O | Me | Me | 3-CF₃-benzyl | 56–58° C. |
| 1.95 | O | Me | Me | 4-CF₃-benzyl | |
| 1.96 | O | Me | Me | 3,4-dichlorobenzyl | |
| 1.97 | O | Me | Me | 2,4,6-trimethylbenzyl | |
| 1.98 | O | Me | Me | 4-chloro-2-nitrobenzyl | |
| 1.99 | O | Me | Me | 3-methoxybenzyl | |
| 1.100 | O | Me | Me | 2-phenethyl | 1.97/2.02 |
| 1.101 | O | Me | Me | 3-phenylpropyl | |
| 1.102 | O | Me | Me | 2-(4-nitrophenyl)ethyl | |
| 1.103 | O | Me | Me | 2-(2-CF₃-phenyl)ethyl | |
| 1.104 | O | Me | Me | 2-(4-methoxy-phenyl)ethyl | |
| 1.105 | O | Me | Me | 2-chloro-6-fluorobenzyl | |
| 1.106 | O | Me | Me | 3,4-methylenedioxy-benzyl | |
| 1.107 | O | Me | Me | 2-cyanobenzyl | |
| 1.108 | O | Me | Me | 2-(4-chlorophenyl)ethyl | |
| 1.109 | O | Me | Me | cyclopropyl-methyl | 2.01/2.01 |
| 1.110 | O | Me | Me | 2-(1,3-dioxolanyl)methyl | |
| 1.111 | O | Me | Me | 2,2,3,3-tetrafluorocyclo-butylmethyl | |
| 1.112 | O | Me | Me | α-fluoroethoxy carbonylmethyl | |
| 1.113 | O | Me | 2-thienyl | Me | 2.06/2.10/2.20 (E/Z) |
| 1.114 | O | Me | 4-methyl-phenyl | Et | 2.12 |
| 1.115 | NMe | Me | 4-methyl-phenyl | Me | 2.10 (isomer1) 2.08 (isomer2) |
| 1.116 | O | Me | Me | CH₂FCH₂ | 50–51° C. |
| 1.117 | O | Me | Me | 2-(4-morpholino)ethyl | 1.99/2.01 |
| 1.118 | — | Me | Me | 1-pyrryl | 89–91° C. |
| 1.119 | O | Me | Me | 2-(1-piperidino)-ethyl | |
| 1.120 | O | Me | Me | 2-fluorobenzyl | 93–96° C. |
| 1.121 | O | Me | Me | 4-fluorobenzyl | 104–106° C. |

**m.p. or ¹H NMR of R₁/R₂ or R₃

TABLE 2

[Structure: H₃C-O-N=C(COOCH₃)-phenyl-CH₂-O-N=C(R₁)-C(R₂)=N-A-R₃]

| Ex. No. | A | R₁ | R₂ | R₃ or NR₃R₄ | Physical data** |
|---|---|---|---|---|---|
| 2.1 | NMe | Me | Me | 6-CF₃-2-pyridyl | |
| 2.2 | NMe | H | Me | 6-CF₃-2-pyridyl | |
| 2.3 | NMe | Me | Δ | 6-CF₃-2-pyridyl | |
| 2.4 | NMe | Me | H | phenyl | |
| 2.5 | NMe | Me | Me | phenyl | 87–88° C. |
| 2.6 | NMe | Δ | Me | phenyl | |
| 2.7 | NMe | Me | Me | 4-CF₃-2-pyridyl | |
| 2.8 | NMe | H | Me | 4-CF₃-2-pyridyl | |
| 2.9 | NMe | Δ | Δ | phenyl | |
| 2.10 | NMe | Me | Me | 5-CF₃-2-pyridyl | |
| 2.11 | NMe | H | Me | 5-CF₃-2-pyridyl | |
| 2.12 | — | H | Me | 4-(1,2,4-triazolyl) | |
| 2.13 | — | Me | Me | 4-(1,2,4-triazolyl) | |
| 2.14 | — | Me | Δ | 4-(1,2,4-triazolyl) | |
| 2.15 | — | Me | Δ | 4-morpholinyl | |
| 2.16 | — | Me | Me | 4-morpholinyl | |
| 2.17 | — | H | Me | 4-morpholinyl | |
| 2.18 | NPh | H | Me | phenyl | |
| 2.19 | NPh | Me | Me | phenyl | 1.64/2.12 |
| 2.20 | NPh | Me | Δ | phenyl | |
| 2.21 | NPh | Δ | Me | phenyl | |
| 2.22 | NMe | Me | Me | 2-nitrophenyl | |
| 2.23 | NMe | H | Me | 2-nitrophenyl | |
| 2.24 | O | Me | Me | Me | 104–106° C. |
| 2.25 | O | H | Me | Me | |
| 2.26 | O | Δ | Me | Me | 1.92/1.97 |
| 2.27 | O | Me | Δ | Me | 67–70° C. |
| 2.28 | O | Me | H | Me | |
| 2.29 | NMe | H | Me | 3-CF₃-2-pyridyl | |
| 2.30 | NMe | Me | Me | 3-CF₃-2-pyridyl | |
| 2.31 | NMe | Δ | Me | 3-CF₃-2-pyridyl | |
| 2.32 | NMe | Δ | Me | 3-nitro-2-pyridyl | |
| 2.33 | NMe | H | Me | 3-nitro-2-pyridyl | |
| 2.34 | NMe | Me | Me | 3-nitro-2-pyridyl | |
| 2.35 | NMe | Me | Me | 2-CF₃-phenyl | |
| 2.36 | NMe | Me | Δ | 2-CF₃-phenyl | |
| 2.37 | NMe | H | Me | 2-CF₃-phenyl | |
| 2.38 | NMe | Me | Me | 3-CF₃-phenyl | |
| 2.39 | NMe | Me | Δ | 3-CF₃-phenyl | |
| 2.40 | NMe | H | Me | 4-CF₃-phenyl | |
| 2.41 | NMe | Me | Me | 4-CF₃-phenyl | |
| 2.42 | NMe | Me | Me | 2-chlorophenyl | 81° C. |

TABLE 2-continued $$\text{structure with } H_3C-O-N=C(COOCH_3)-\text{phenyl}-CH_2-O-N=C(R_1)-C(R_2)=N-A-R_3$$

| Ex. No. | A | $R_1$ | $R_2$ | $R_3$ or $NR_3R_4$ | Physical data** |
|---|---|---|---|---|---|
| 2.43 | NMe | Me | Me | 3-chlorophenyl | 2.10/2.13 |
| 2.44 | NMe | H | Me | 4-chlorophenyl | |
| 2.45 | NMe | Me | Me | 4-chlorophenyl | 2.08/2.13 |
| 2.46 | O | Me | Me | phenyl | 89–90° C. |
| 2.47 | O | Me | Δ | phenyl | |
| 2.48 | O | Me | Me | benzyl | |
| 2.49 | O | Me | Me | Et | |
| 2.50 | O | H | Me | Et | |
| 2.51 | O | Δ | Me | Et | |
| 2.52 | O | Me | Δ | Et | |
| 2.53 | O | Me | H | Et | |
| 2.54 | O | H | Me | methoxymethyl | |
| 2.55 | O | Me | Me | methoxymethyl | 87–88° C. |
| 2.56 | O | Me | Δ | methoxymethyl | |
| 2.57 | O | Δ | Me | methoxymethyl | |
| 2.58 | O | Me | Me | ethoxymethyl | |
| 2.59 | O | H | Me | cyanomethyl | |
| 2.60 | O | Me | Me | cyanomethyl | 94–95° C. |
| 2.61 | O | Δ | Me | cyanomethyl | |
| 2.62 | — | Me | Me | azepino | |
| 2.63 | — | Me | Me | piperidino | |
| 2.64 | — | Me | Me | pyrrolidino | |
| 2.65 | O | H | Me | tert-butyl | |
| 2.66 | O | Me | Me | tert-butyl | 1.93/2.02 |
| 2.67 | O | Me | Me | propargyl | 120–122° C. |
| 2.68 | O | Δ | Me | propargyl | |
| 2.69 | O | Me | Δ | propargyl | |
| 2.70 | O | Me | Me | 2,2-dichloro-cyclo-propylmethyl | 1.99/1.99 |
| 2.71 | O | Δ | Me | 2,2-dichlorocyclo-propylmethyl | |
| 2.72 | O | H | Me | H | |
| 2.73 | O | Me | Me | H | 114–116° C. |
| 2.74 | O | Me | Me | $CF_3CH_2$ | 52–53° C. |
| 2.75 | O | Δ | Me | $CF_3CH_2$ | |
| 2.76 | O | Me | H | $CF_3CH_2$ | |
| 2.77 | O | Me | H | $CF_3CH_2CH_2$ | |
| 2.78 | O | Me | Me | $CF_3CH_2CH_2$ | |
| 2.79 | O | Me | Me | $CF_3CH_2CH_2CH_2$ | 86° C. |
| 2.80 | O | Δ | Me | $CF_3CH_2CH_2CH_2$ | |
| 2.81 | NMe | Me | Me | Me | 80–81° C. |
| 2.82 | NMe | Me | Δ | Me | |
| 2.83 | O | Me | Me | $CH_2\text{'}_{-CCl=CH_2}$ | 66° C. |
| 2.84 | O | Δ | Me | $CH_2\text{'}_{-CCl=CH_2}$ | |
| 2.85 | O | Me | Me | propyl | |
| 2.86 | O | Me | Me | butyl | 58–62° C. |
| 2.87 | O | Me | Me | hexyl | 50–53° C. |
| 2.88 | O | Me | Me | methoxycarbonyl-methyl | 1.96/2.04 |
| 2.89 | O | H | Me | methoxycarbonyl-methyl | |
| 2.90 | O | Me | Me | 3-fluorobenzyl | |
| 2.91 | O | Me | Me | 4-chlorobenzyl | |
| 2.92 | O | Me | Me | 2-chlorobenzyl | |
| 2.93 | O | Me | Me | 2-$CF_3$-benzyl | |
| 2.94 | O | Me | Me | 3-$CF_3$-benzyl | 87–88° C. |
| 2.95 | O | Me | Me | 4-$CF_3$-benzyl | |
| 2.96 | O | Me | Me | 3,4-dichlorobenzyl | |
| 2.97 | O | Me | Me | 2,4,6-trimethylbenzyl | |
| 2.98 | O | Me | Me | 4-chloro-2-nitrobenzyl | |
| 2.99 | O | Me | Me | 3-methoxybenzyl | |
| 2.100 | O | Me | Me | 2-phenethyl | |
| 2.101 | O | Me | Me | 3-phenylpropyl | |
| 2.102 | O | Me | Me | 2-(4-nitrophenyl)ethyl | |
| 2.103 | O | Me | Me | 2-(2-$CF_3$-phenyl)ethyl | |
| 2.104 | O | Me | Me | 2-(4-methoxy-phenyl)ethyl | |
| 2.105 | O | Me | Me | 2-chloro-6-fluorobenzyl | |
| 2.106 | O | Me | Me | 3,4-methylenedioxy-benzyl | |
| 2.107 | O | Me | Me | 2-cyanobenzyl | |
| 2.108 | O | Me | Me | 2-(4-chlorophenyl)ethyl | |
| 2.109 | O | Me | Me | cyclopropylmethyl | |
| 2.110 | O | Me | Me | 2-(1,3-dioxolanyl)methyl | 1.98/1.98 |
| 2.111 | O | Me | Me | 2,2,3,3-tetrafluorcyclo-butylmethyl | |
| 2.112 | O | Me | Me | α-fluoroethoxy-carbonylmethyl | |
| 2.113 | O | Me | 2-thienyl | Me | 83–86° C. |
| 2.114 | O | Me | 4-methyl-phenyl | Et | 94–96° C. |
| 2.115 | NMe | Me | 4-methyl-phenyl | Me | |
| 2.116 | O | Me | Me | $CH_2FCH_2$ | 62–63° C. |
| 2.117 | O | Me | Me | 2-(4-morpho-lino)ethyl | 1.97/1.99 |
| 2.118 | — | Me | Me | 1-pyrryl | |
| 2.119 | O | Me | Me | 2-(1-piperidino)-ethyl | 1.95/2.00 |
| 2.120 | O | Me | Me | 2-fluorobenzyl | 81–83° C. |
| 2.121 | O | Me | Me | 4-fluorobenzyl | 116–118° C. |

**m.p. or $^1$H NMR of $R_1/R_2$ or $R_3$

TABLE 3

$$\text{structure with } H_3C-O-N=C(CONHCH_3)-\text{phenyl}-CH_2-O-N=C(R_1)-C(R_2)=N-A-R_3$$

| Ex. No. | A | $R_1$ | $R_2$ | $R_3$ or $NR_3R_4$ | Physical data** |
|---|---|---|---|---|---|
| 3.1 | NMe | Me | Me | 6-$CF_3$-2-pyridyl | |
| 3.2 | NMe | H | Me | 6-$CF_3$-2-pyridyl | |
| 3.3 | NMe | Me | Δ | 6-$CF_3$-2-pyridyl | |
| 3.4 | NMe | Me | H | phenyl | |
| 3.5 | NMe | Me | Me | phenyl | 2.07/2.15 |
| 3.6 | NMe | Δ | Me | phenyl | |
| 3.7 | NMe | Me | Me | 4-$CF_3$-2-pyridyl | |
| 3.8 | NMe | H | Me | 4-$CF_3$-2-pyridyl | |
| 3.9 | NMe | Δ | Δ | phenyl | |
| 3.10 | NMe | Me | Me | 5-$CF_3$-2-pyridyl | |
| 3.11 | NMe | H | Me | 5-$CF_3$-2-pyridyl | |
| 3.12 | — | H | Me | 4-(1,2,4-triazolyl) | |
| 3.13 | — | Me | Me | 4-(1,2,4-triazolyl) | |
| 3.14 | — | Me | Δ | 4-(1,2,4-triazolyl) | |
| 3.15 | — | Me | Δ | 4-morpholinyl | |
| 3.16 | — | Me | Me | 4-morpholinyl | |
| 3.17 | — | H | Me | 4-morpholinyl | |
| 3.18 | NPh | H | Me | phenyl | |
| 3.19 | NPh | Me | Me | phenyl | 135–136° C. |
| 3.20 | NPh | Me | Δ | phenyl | |
| 3.21 | NPh | Δ | Me | phenyl | |
| 3.22 | NMe | Me | Me | 2-nitrophenyl | |

TABLE 3-continued

| Ex. No. | A | $R_1$ | $R_2$ | $R_3$ or $NR_3R_4$ | Physical data** |
|---|---|---|---|---|---|
| 3.23 | NMe | H | Me | 2-nitrophenyl | |
| 3.24 | O | Me | Me | Me | 90–92° C. |
| 3.25 | O | H | Me | Me | 1.97/7.68 |
| 3.26 | O | Δ | Me | Me | 1.94/1.95 |
| 3.27 | O | Me | Δ | Me | 88–90° C. |
| 3.28 | O | Me | H | Me | |
| 3.29 | NMe | H | Me | 3-$CF_3$-2-pyridyl | |
| 3.30 | NMe | Me | Me | 3-$CF_3$-2-pyridyl | |
| 3.31 | NMe | Δ | Me | 3-$CF_3$-2-pyridyl | |
| 3.32 | NMe | Δ | Me | 3-nitro-2-pyridyl | |
| 3.33 | NMe | H | Me | 3-nitro-2-pyridyl | |
| 3.34 | NMe | Me | Me | 3-nitro-2-pyridyl | |
| 3.35 | NMe | Me | Me | 2-$CF_3$-phenyl | |
| 3.36 | NMe | Me | Δ | 2-$CF_3$-phenyl | |
| 3.37 | NMe | H | Me | 2-$CF_3$-phenyl | |
| 3.38 | NMe | Me | Me | 3-$CF_3$-phenyl | |
| 3.39 | NMe | Me | Δ | 3-$CF_3$-phenyl | |
| 3.40 | NMe | H | Me | 4-$CF_3$-phenyl | |
| 3.41 | NMe | Me | Me | 4-$CF_3$-phenyl | |
| 3.42 | NMe | Me | Me | 2-chlorophenyl | 1.72/2.11 |
| 3.43 | NMe | Me | Me | 3-chlorophenyl | 2.09/2.14 |
| 3.44 | NMe | H | Me | 4-chlorophenyl | |
| 3.45 | NMe | Me | Me | 4-chlorophenyl | 2.08/2.13 |
| 3.46 | O | Me | Me | phenyl | |
| 3.47 | O | Me | Δ | phenyl | |
| 3.48 | O | Me | Me | benzyl | |
| 3.49 | O | Me | Me | Et | |
| 3.50 | O | H | Me | Et | |
| 3.51 | O | Δ | Me | Et | |
| 3.52 | O | Me | Δ | Et | |
| 3.53 | O | Me | H | Et | |
| 3.54 | O | H | Me | methoxymethyl | |
| 3.55 | O | Me | Me | methoxymethyl | 2.00/2.03 |
| 3.56 | O | Me | Δ | methoxymethyl | |
| 3.57 | O | Δ | Me | methoxymethyl | |
| 3.58 | O | Me | Me | ethoxymethyl | |
| 3.59 | O | H | Me | cyanomethyl | |
| 3.60 | O | Me | Me | cyanomethyl | 2.00/2.01 |
| 3.61 | O | Δ | Me | cyanomethyl | |
| 3.62 | — | Me | Me | azepino | |
| 3.63 | — | Me | Me | piperidino | |
| 3.64 | — | Me | Me | pyrrolidino | |
| 3.65 | O | H | Me | tert-butyl | |
| 3.66 | O | Me | Me | tert-butyl | 1.95/2.01 |
| 3.67 | O | Me | Me | propargyl | 114–115° C. |
| 3.68 | O | Δ | Me | propargyl | |
| 3.69 | O | Me | Δ | propargyl | |
| 3.70 | O | Me | Me | 2,2-dichloro-cyclopropyl-methyl | |
| 3.71 | O | Δ | Me | 2,2-dichloro-cyclopropyl-methyl | |
| 3.72 | O | H | Me | H | |
| 3.73 | O | Me | Me | H | 137° C. |
| 3.74 | O | Me | Me | $CF_3CH_2$ | 94–96° C. |
| 3.75 | O | Δ | Me | $CF_3CH_2$ | |
| 3.76 | O | Me | H | $CF_3CH_2$ | |
| 3.77 | O | Me | H | $CF_3CH_2CH_2$ | |
| 3.78 | O | Me | Me | $CF_3CH_2CH_2$ | |
| 3.79 | O | Me | Me | $CF_3CH_2CH_2CH_2$ | |
| 3.80 | O | Δ | Me | $CF_3CH_2CH_2CH_2$ | |
| 3.81 | NMe | Me | Me | Me | 90–91° C. |
| 3.82 | NMe | Me | Δ | Me | |
| 3.83 | O | Me | Me | $CH_2\text{-}CCl=CH_2$ | 1.97/2.02 |
| 3.84 | O | Δ | Me | $CH_2\text{-}CCl=CH_2$ | |
| 3.85 | O | Me | Me | propyl | |
| 3.86 | O | Me | Me | butyl | 91–92° C. |
| 3.87 | O | Me | Me | hexyl | 84–86° C. |
| 3.88 | O | Me | Me | methylcarbamoyl-methyl | 127–129° C. |
| 3.89 | O | H | Me | methoxycarbonyl-methyl | |
| 3.90 | O | Me | Me | 3-fluorobenzyl | |
| 3.91 | O | Me | Me | 4-chlorobenzyl | |
| 3.92 | O | Me | Me | 2-chlorobenzyl | |
| 3.93 | O | Me | Me | 2-$CF_3$-benzyl | |
| 3.94 | O | Me | Me | 3-$CF_3$-benzyl | 1.96/2.00 |
| 3.95 | O | Me | Me | 4-$CF_3$-benzyl | |
| 3.96 | O | Me | Me | 3,4-dichlorobenzyl | |
| 3.97 | O | Me | Me | 2,4,6-trimethylbenzyl | |
| 3.98 | O | Me | Me | 4-chloro-2-nitrobenzyl | |
| 3.99 | O | Me | Me | 3-methoxybenzyl | |
| 3.100 | O | Me | Me | 2-phenethyl | |
| 3.101 | O | Me | Me | 3-phenylpropyl | |
| 3.102 | O | Me | Me | 2-(4-nitrophenyl)ethyl | |
| 3.103 | O | Me | Me | 2-(2-$CF_3$-phenyl)ethyl | |
| 3.104 | O | Me | Me | 2-(4-methoxy-phenyl)ethyl | |
| 3.105 | O | Me | Me | 2-chloro-6-fluorobenzyl | |
| 3.106 | O | Me | Me | 3,4-methylenedioxy-benzyl | |
| 3.107 | O | Me | Me | 2-cyanobenzyl | |
| 3.108 | O | Me | Me | 2-(4-chlorophenyl)ethyl | |
| 3.109 | O | Me | Me | cyclopropylmethyl | 2.00/2.00 |
| 3.110 | O | Me | Me | 2-(1,3-dioxolanyl)methyl | |
| 3.111 | O | Me | Me | 2,2,3,3-tetrafluorocyclo-butylmethyl | |
| 3.112 | O | Me | Me | α-fluoroethoxy-carbonylmethyl | |
| 3.113 | O | Me | 2-thienyl | Me | |
| 3.114 | O | Me | 4-methyl-phenyl | Et | 103-104° C. |
| 3.115 | NMe | Me | 4-methyl-phenyl | Me | |
| 3.116 | O | Me | Me | $CH_2FCH_2$ | 95–97° C. |
| 3.117 | O | Me | Me | 2-(4-morpho-lino)ethyl | 1.98/2.06 |
| 3.118 | — | Me | Me | 1-pyrryl | |
| 3.119 | O | Me | Me | 2-(1-piperidino)-ethyl | 1.96/1.98 |
| 3.120 | O | Me | Me | 2-fluorobenzyl- | 90–91° C. |
| 3.121 | O | Me | Me | 4-fluorobenzyl | 130–131° C. |

**m.p. or $^1$H NMR of $R_1/R_2$ or $R_3$

TABLE 4

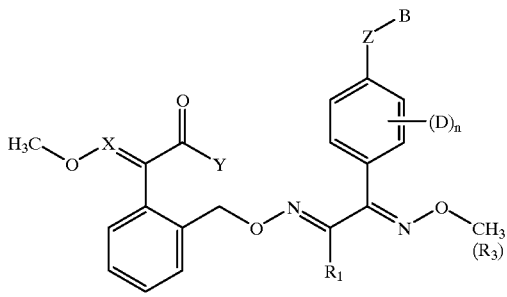

| Ex. | X | Y | R₁ | Z* | n | B or D | Physical data** |
|---|---|---|---|---|---|---|---|
| 4.1 | CH | OMe | Me | — | 1 | 3-CF₃ | 133–135° C. |
| 4.2 | CH | OMe | Me | — | 1 | 4-chloro | 140–142° C. |
| 4.3 | CH | OMe | Me | — | 1 | 3-chloro | 175–177° C. |
| 4.4 | CH | OMe | Me | — | 1 | 2-fluoro | 136–137° C. |
| 4.5 | CH | OMe | Me | — | 1 | 4-methyl | isom.1: 98–101° C. |
| | | | | | | | isom.2: oil |
| | | | | | | | isom.3: oil |
| 4.6 | CH | OMe | Me | O | 0 | methyl- | 104–106° C. |
| 4.7 | CH | OMe | Me | — | 1 | 4-bromo | 126–128° C. |
| 4.8 | CH | OMe | Me | — | 1 | 4-fluoro | 141–144° C. |
| 4.9 | CH | OMe | Me | — | 2 | 3-F-5-CF₃ | 164–166° C. |
| 4.10 | CH | OMe | Me | — | 0 | — | 141–143° C. |
| 4.11 | CH | OMe | Me | — | 1 | 2-methyl | 113–115° C. |
| 4.12 | CH | OMe | Me | — | 1 | 3-bromo | 176–178° C. |
| 4.13 | CH | OMe | Me | — | 2 | 3,4-methylenedioxy | 143–145° C. |
| 4.14 | CH | OMe | Me | O | 0 | allyl- | 77–80° C. (isomer1) |
| | | | | | | | 2.08 (isomer2) |
| 4.15 | CH | OMe | SMe | — | 1 | 4-methyl | 2.08 (isomer1) |
| | | | | | | | 2.11 (isomer2) |
| 4.16 | CH | OMe | Et | — | 1 | 4-methyl | 3.90 (isomer1) |
| | | | | | | | 3.97 (isomer2) |
| 4.17 | CH | OMe | Me | — | 1 | 4-isobutyl- | 2.11 (isomer1) |
| | | | | | | | 2.08 (isomer2) |
| 4.18 | CH | OMe | Me | O | 0 | propargyl- | 2.06/2.11 (E/Z) |
| 4.19 | CH | OMe | Me | O | 0 | 2,2,2-trifluoroethyl | 2.11 (isomer1) |
| | | | | | | | 2.07 (isomer2) |
| 4.20 | CH | OMe | Me | O | 0 | ethyl | 93-95° C. (isomer1) |
| | | | | | | | 2.06 (isomer2) |
| 4.21 | CH | OMe | CN | — | 1 | 4-methyl | 98–133° C. (E/Z) |
| 4.22 | CH | OMe | CN | — | 1 | 4-chloro | 106–108° C. |
| 4.23 | CH | OMe | CN | — | 2 | 3,4-dichloro | 128–130° C. |
| | | | | | | | 109–111° C. (E/Z) |
| 4.24 | CH | OMe | CN | O | 0 | —CF₃ | oil (E/Z) |
| 4.25 | CH | OMe | CN | — | 1 | 3-CF₃ | |
| 4.26 | CH | OMe | CN | — | 1 | 2-chloro | |
| 4.27 | CH | OMe | CN | — | 1 | 4-fluoro | |
| 4.28 | CH | OMe | Me | O | 0 | phenyl | 112–114° C. (iso.1) |
| | | | | | | | oil (iso.2) |
| 4.29 | CH | OMe | Me | O | 0 | —CH₂CH=CCl₂ | |
| 4.30 | CH | OMe | Me | O | 0 | CH₂—CH=CF₂ | |
| 4.31 | CH | OMe | Me | O | 0 | —CH₂CH=CBr₂ | |
| 4.32 | CH | OMe | Me | O | 0 | 4-Cl-phenyl | isomer 1: oil |
| | | | | | | | isomer 2: resin |
| 4.33 | CH | OMe | Me | O | 0 | 4-F-phenyl | isomer 1: 126–128° C. |
| | | | | | | | isomer 2: oil |
| 4.34 | CH | OMe | Me | S | 0 | phenyl | isomer 1: oil |
| | | | | | | | isomer 2: oil |
| 4.35 | CH | OMe | Me | —CH₂O— | 0 | phenyl*** | isomer 1: resin |
| | | | | | | | isomer 2: resin |
| 4.36 | CH | OMe | Me | —OCH₂— | 0 | phenyl*** | oil |
| 4.37 | N | OMe | Me | — | 1 | 3-CF₃ | |
| 4.38 | N | OMe | Me | — | 1 | 4-chloro | |
| 4.39 | N | OMe | Me | — | 1 | 3-chloro | |
| 4.40 | N | OMe | Me | — | 1 | 2-fluoro | 111–112° C. |
| 4.41 | N | OMe | Me | — | 1 | 4-methyl | 101–103° C. |
| 4.42 | N | OMe | Me | O | 0 | 4-methyl- | 104–106° C. |
| 4.43 | N | OMe | Me | — | 1 | 4-bromo | 134–136° C. |
| 4.44 | N | OMe | Me | — | 1 | 4-fluoro | |
| 4.45 | N | OMe | Me | — | 2 | 3-F-5-CF₃ | |
| 4.46 | N | OMe | Me | — | 0 | — | |

TABLE 4-continued

| Ex. | X | Y | R$_1$ | Z* | n | B or D | Physical data** |
|---|---|---|---|---|---|---|---|
| 4.47 | N | OMe | Me | — | 1 | 2-methyl | 105–107° C. |
| 4.48 | N | OMe | Me | — | 1 | 3-bromo | |
| 4.49 | N | OMe | Me | — | 2 | 3,4-methylenedioxy | |
| 4.50 | N | OMe | Me | O | 0 | allyl | 74–76° C. |
| 4.51 | N | OMe | SMe | — | 1 | 4-methyl | 88–91° C. |
| 4.52 | N | OMe | Et | — | 1 | 4-methyl | |
| 4.53 | N | OMe | Me | — | 1 | 4-isobutyl- | |
| 4.54 | N | OMe | Me | O | 0 | propargyl | oil |
| 4.55 | N | OMe | Me | O | 0 | 2,2,2-trifluoroethyl | |
| 4.56 | N | OMe | Me | O | 0 | ethyl | oil |
| 4.57 | N | OMe | CN | — | 1 | 4-methyl | |
| 4.58 | N | OMe | CN | — | 1 | 4-chloro | |
| 4.59 | N | OMe | CN | — | 2 | 3,4-dichloro | |
| 4.60 | N | OMe | CN | O | 0 | —CF$_3$ | |
| 4.61 | N | OMe | CN | — | 1 | 3-CF$_3$ | |
| 4.62 | N | OMe | CN | — | 1 | 2-chloro | |
| 4.63 | N | OMe | CN | — | 1 | 4-fluoro | |
| 4.64 | N | OMe | Me | O | 0 | phenyl | |
| 4.65 | N | OMe | Me | O | 0 | —CH$_2$CH=CCl$_2$ | |
| 4.66 | N | OMe | Me | O | 0 | —CH$_2$CH=CF$_2$ | |
| 4.67 | N | OMe | Me | O | 0 | —CH$_2$CH=CBr$_2$ | |
| 4.68 | N | OMe | Me | O | 0 | 4-Cl-phenyl | 120–122° C. |
| 4.69 | N | OMe | Me | O | 0 | 4-F-phenyl | 130–132° C. |
| 4.70 | N | OMe | Me | S | 0 | phenyl | |
| 4.71 | N | OMe | Me | —CH$_2$O— | 0 | phenyl*** | |
| 4.72 | N | OMe | Me | —OCH$_2$— | 0 | phenyl*** | |
| 4.73 | N | NHCH$_3$ | Me | — | 1 | 3-CF$_3$ | |
| 4.74 | N | NHCH$_3$ | Me | — | 1 | 4-chloro | |
| 4.75 | N | NHCH$_3$ | Me | — | 1 | 3-chloro | |
| 4.76 | N | NHCH$_3$ | Me | — | 1 | 2-fluoro | 2.11 |
| 4.77 | N | NHCH$_3$ | Me | — | 1 | 4-methyl | 2.10 |
| 4.78 | N | NHCH$_3$ | Me | O | 0 | methyl- | |
| 4.79 | N | NHCH$_3$ | Me | — | 1 | 4-bromo | 2.09 |
| 4.80 | N | NHCH$_3$ | Me | — | 1 | 4-fluoro | |
| 4.81 | N | NHCH$_3$ | Me | — | 2 | 3-fluoro-5-CF$_3$ | |
| 4.82 | N | NHCH$_3$ | Me | — | 0 | — | |
| 4.83 | N | NHCH$_3$ | Me | — | 1 | 2-methyl | 2.05 |
| 4.84 | N | NHCH$_3$ | Me | — | 1 | 3-bromo | |
| 4.85 | N | NHCH$_3$ | Me | — | 2 | 3,4-methylenedioxy | |
| 4.86 | N | NHCH$_3$ | Me | O | 0 | allyl | 118–120° C. |
| 4.87 | N | NHCH$_3$ | SMe | — | 1 | 4-methyl | 2.06 |
| 4.88 | N | NHCH$_3$ | Et | — | 1 | 4-methyl | |
| 4.89 | N | NHCH$_3$ | Me | — | 1 | 4-isobutyl- | |
| 4.90 | N | NHCH$_3$ | Me | O | 0 | propargyl | oil |
| 4.91 | N | NHCH$_3$ | Me | O | 0 | 2,2,2-trifluoroethyl | |
| 4.92 | N | NHCH$_3$ | Me | O | 0 | ethyl | oil |
| 4.93 | N | NHCH$_3$ | CN | — | 1 | 4-methyl | |
| 4.94 | N | NHCH$_3$ | CN | — | 1 | 4-chloro | |
| 4.95 | N | NHCH$_3$ | CN | — | 2 | 3,4-dichloro | |
| 4.96 | N | NHCH$_3$ | CN | O | 0 | —CF$_3$ | |
| 4.97 | N | NHCH$_3$ | CN | — | 1 | 3-CF$_3$ | |
| 4.98 | N | NHCH$_3$ | CN | — | 1 | 2-chloro | |
| 4.99 | N | NHCH$_3$ | CN | — | 1 | 4-fluoro | |
| 4.100 | N | NHCH$_3$ | Me | O | 0 | phenyl | |
| 4.101 | N | NHCH$_3$ | Me | O | 0 | —CH$_2$CH=CCl$_2$ | |
| 4.102 | N | NHCH$_3$ | Me | O | 0 | —CH$_2$CH=CF$_2$ | |
| 4.103 | N | NHCH$_3$ | Me | O | 0 | —CH$_2$CH=CBr$_2$ | |
| 4.104 | N | NHCH$_3$ | Me | O | 0 | 4-Cl-phenyl | resin |
| 4.105 | N | NHCH$_3$ | Me | O | 0 | 4-F-phenyl | |
| 4.106 | N | NHCH$_3$ | Me | S | 0 | phenyl | |
| 4.107 | N | NHCH$_3$ | Me | —CH$_2$O— | 0 | phenyl | *** |

TABLE 4-continued

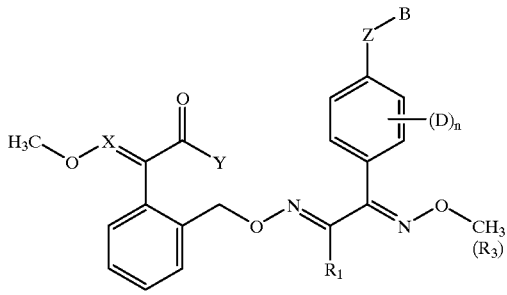

| Ex. | X | Y | R₁ | Z* | n | B or D | Physical data** |
|---|---|---|---|---|---|---|---|
| 4.108 | N | NHCH₃ | Me | —OCH₂— | 0 | phenyl | *** |
| 4.109 | CH | OCH₃ | Me | O | 0 | n-propyl | isomer 1: oil<br>isomer 2: oil |
| 4.110 | CH | OCH₃ | Me | O | 0 | 3,3-dimethyl allyl | 107–110° C. (iso 1)<br>oil (iso 2) |
| 4.111 | CH | OCH₃ | Me | O | 0 | 2-methyl-allyl | isomer 1: 97–99° C.<br>isomer 2: oil |
| 4.112 | CH | OCH₃ | Me | O | 0 | 3-methyl-allyl | isomer 1: oil<br>isomer 2: oil |
| 4.113 | CH | OCH₃ | Me | O | 0 | allyl | isomer 1: 74–76° C. |
| 4.114 | CH | OCH₃ | Me | O | 0 | propargyl | oil |
| 4.115 | CH | NHCH₃ | Me | O | 0 | allyl | |
| 4.116 | CH | NHCH₃ | Me | O | 0 | propargyl | |
| 4.117 | CH | OCH₃ | Me | —OCH₂— | 0 | 3-CF₃-phenyl *** | isomer 1: 83-85° C.<br>isomer 2: resin |
| 4.118 | CH | OCH₃ | Me | O | 0 | 3-CF₃-phenyl | isomer 1: 127–128<br>isomer 2: oil |
| 4.119 | CH | OCH₃ | Me | —OCH₂— | 0 | C₆H₁₁*** | isomer 1: oil<br>isomer 2: oil |
| 4.120 | CH | OCH₃ | Me | —OCH₂— | 0 | phenyl*** | isomer 1: oil<br>isomer 2: oil |
| 4.121 | CH | OCH₃ | Me | —OCH₂— | 0 | 4-F-phenyl *** | isomer 1: oil<br>isomer 2: oil |
| 4.122 | CH | OCH₃ | Me | S | 0 | CH₃ | isomer 1: 119–121° C.<br>isomer 2: resin |
| 4.123 | CH | OCH₃ | Me | —SO₂— | 0 | CH₃ | isomer 1: foam<br>isomer 2: resin |
| 4.124 | CH | OCH₃ | Me | —CH₂O— | 0 | phenyl*** | isomer 1: oil<br>isomer 2: resin |
| 4.125 | CH | OCH₃ | Me | —OCH₂— | 0 | 4-CF₃-phenyl*** | isomer 1: 82–84° C.<br>isomer 2: 89–91° C. |
| 4.126 | CH | OCH₃ | Me | —OCH₂— | 0 | 4-Br-phenyl*** | |
| 4.127 | CH | OCH₃ | Me | —OCH₂— | 0 | 4-CH₃-phenyl*** | |
| 4.128 | CH | OCH₃ | Me | —OCH₂— | 0 | 4-OCH₃-phenyl*** | |
| 4.129 | CH | OCH₃ | Me | —OCH₂— | 0 | 2-CF₃-phenyl*** | isomer 1: 125–129° C.<br>isomer 2: resin |
| 4.130 | CH | OCH₃ | Me | —OCH₂— | 0 | 2-F-phenyl*** | isomer 1: oil<br>isomer 2: oil |
| 4.131 | CH | OCH₃ | Me | —OCH₂— | 0 | 2-Cl-phenyl*** | |
| 4.132 | CH | OCH₃ | Me | —OCH₂— | 0 | 2-Br-phenyl*** | |
| 4.133 | CH | OCH₃ | Me | —OCH₂— | 0 | 3-F-phenyl*** | isomer 1: 111–112° C.<br>isomer 2: oil |
| 4.134 | CH | OCH₃ | Me | —OCH₂— | 0 | 3-Cl-phenyl*** | isomer 1: oil<br>isomer 2: oil |
| 4.135 | CH | OCH₃ | Me | —OCH₂— | 0 | 3-Br-phenyl*** | isomer 1: resin<br>isomer 2: Harz |
| 4.136 | N | OCH₃ | Me | —OCH₂— | 0 | allyl*** | |
| 4.137 | N | OCH₃ | Me | —OCH₂— | 0 | 3-CF₃-phenyl*** | |
| 4.138 | N | NHCH₃ | Me | —OCH₂— | 0 | 3-CF₃-phenyl*** | |
| 4.139 | N | OCH₃ | Me | — | 1 | 2-CF₃ | oil |
| 4.140 | N | OCH₃ | Me | — | 1 | 2-CH₃ | isomer 1: 105–107° C.<br>isomer 2: resin |
| 4.141 | N | NHCH₃ | Me | — | 1 | 2-CF₃ | resin |
| 4.142 | N | NHCH₃ | Me | — | 1 | 2-CH₃ | isomer 1: oil<br>isomer 2: oil |
| 4.143 | CH | OCH₃ | CN | — | — | H | oil |
| 4.144 | CH | OCH₃ | CN | O | 0 | CH₃ | isomer 1: 136–138° C.<br>isomer 2: resin |
| 4.145 | CH | OCH₃ | CN | — | 1 | 4-t-butyl | oil |
| 4.146 | CH | OCH₃ | CN | O | 0 | phenyl | oil |
| 4.147 | CH | OCH₃ | Me | O | 0 | CF₂CHF₂ | isomer 1: 80–82° C. |

TABLE 4-continued

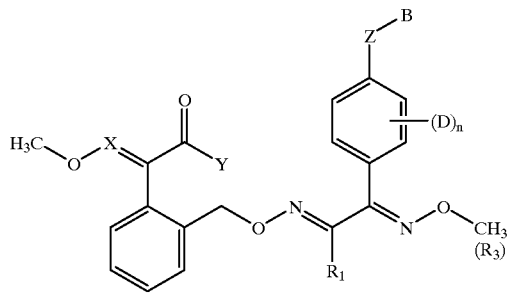

| Ex. | X | Y | $R_1$ | Z* | n | B or D | Physical data** |
|---|---|---|---|---|---|---|---|
| | | | | | | | isomer 2: oil |
| 4.148 | CH | $OCH_3$ | Me | O | 0 | $CF_2CHCl_2$ | |
| 4.149 | CH | $OCH_3$ | Me | O | 0 | $CF_2CHBr_2$ | |
| 4.150 | N | $OCH_3$ | Me | O | 0 | $CF_2CHFCF_3$ | 68–70° C. |
| 4.151 | N | $OCH_3$ | Me | O | 0 | $CF_2CHF_2$ | 96–98° C. |
| 4.152 | N | $OCH_3$ | Me | O | 0 | $CF_2CHFCF_3$ | |
| 4.153 | N | $NHCH_3$ | Me | O | 0 | $CF_2CHF_2$ | 114–116° C. |
| 4.154 | N | $NHCH_3$ | Me | O | 0 | $CF_2CHFCF_3$ | |
| 4.155 | CH | $OCH_3$ | Me | — | 1 | 4-ethyl | isomer 1: oil |
| | | | | | | | isomer 2: oil |
| 4.156 | CH | $OCH_3$ | Me | — | 1 | 4-t-butyl | isomer 1: resin |
| | | | | | | | isomer 2: oil |
| 4.157 | CH | $OCH_3$ | Me | — | 1 | 4-$CF_3$ | isomer 1: resin |
| | | | | | | | isomer 2: 101–102° C. |
| 4.158 | CH | $OCH_3$ | Me | —$OCH_2$— | 1 | 4-Cl-phenyl*** | |
| 4.159 | CH | OMe | CN | O | 0 | phenyl | |
| 4.160 | N | $OCH_3$ | Me | —$SO_2$— | 0 | Et | foam |
| 4.161 | N | $NHCH_3$ | Me | —$SO_2$ | 0 | Et | 141–143° C. |
| 4.162 | CH | $OCH_3$ | Me | —$OCH_2$— | 0 | $SiMe_3$ | isomer 1: resin |
| | | | | | | | isomer 2: oil |
| 4.163 | CH | $OCH_3$ | Me | O | 0 | $CF_2CHFCl$ | isomer 1: 75–76° C. |
| 4.164 | CH | $OCH_3$ | Me | O | 0 | $CF_2CHFBr$ | isomer 1: resin |
| 4.165 | CH | $OCH_3$ | Me | O | 0 | $CF_2CHFCF_3$ | isomer 1: 82–84° C. |
| 4.166 | CH | $OCH_3$ | Me | S | 0 | Et | isomer 1: oil |
| | | | | | | | isomer 2: oil |
| 4.167 | CH | $OCH_3$ | Me | S | 0 | n-$C_3H_7$ | isomer 1: oil |
| | | | | | | | isomer 2: oil |
| 4.168 | CH | $OCH_3$ | Me | —$SCH_2$— | 0 | 3-$CF_3$-phenyl | |
| 4.169 | CH | $OCH_3$ | Me | —$SO_2CH_2$— | 0 | 3-$CF_3$-phenyl | |
| | | | | | | B | D |
| 4.170 | CH | $OCH_3$ | Me | —$SO_2CH_2$— | 1 | 3-$CF_3$-phenyl | 3-F # |
| | | | | | | | #isom.1: 112–114° |
| | | | | | | | #isomer 2: resin |

*The character "—" in column Z means the compound does not have a substituent —Z—B.

**Physical data: m.p. or $^1$H NMR of $R_1$ or $R_3$, $R_3$ always being $CH_3$ in accordance with the structural formula in the heading of the table.

***The radicals Z are to be read in such a manner that the skeleton of the structure is on the left of the structural element in question, while the substituent B is on the right. For example, the substituent Z—B in compound 4.107 is —$CH_2$O-phenyl.

TABLE 5

[Structure: H3C-O-N=C(X)-C(=O)-Y attached to benzene-CH2-O-N=C(R1)- connected to C(=N-A-R3) and phenyl-O-(CH2)p-cyclopropyl(R6,R7,H,H)]

| Ex. No. | X | Y | A | R₁ | R₃ | R₆ | R₇ | p | Physical data |
|---|---|---|---|---|---|---|---|---|---|
| 5.1 | CH | OCH₃ | NMe | Me | Me | Cl | Cl | 1 | |
| 5.2 | CH | OCH₃ | NMe | H | Me | Cl | Cl | 1 | |
| 5.3 | CH | OCH₃ | NMe | Me | Me | F | F | 1 | |
| 5.4 | CH | OCH₃ | NMe | Me | Et | F | F | 1 | |
| 5.5 | CH | OCH₃ | NMe | Me | Me | Br | Br | 1 | |
| 5.6 | CH | OCH₃ | NPh | Me | Me | Cl | Cl | 1 | |
| 5.7 | CH | OCH₃ | NPh | H | Me | Cl | Cl | 1 | |
| 5.8 | CH | OCH₃ | NPh | Me | Et | Cl | Cl | 1 | |
| 5.9 | CH | OCH₃ | O | Me | Me | Cl | Cl | 1 | isom.1: 86–88° C. isom.2: resin isom.3: resin |
| 5.10 | CH | OCH₃ | O | H | Me | Cl | Cl | 1 | |
| 5.11 | CH | OCH₃ | O | Me | Me | F | F | 1 | |
| 5.12 | CH | OCH₃ | O | H | Me | F | F | 1 | |
| 5.13 | CH | OCH₃ | O | Me | H | F | F | 1 | |
| 5.14 | CH | OCH₃ | O | Me | C₃H₇ | Cl | Cl | 1 | |
| 5.15 | CH | OCH₃ | O | Me | Δ | Cl | Cl | 1 | |
| 5.16 | CH | OCH₃ | O | Δ | Me | Cl | Cl | 1 | |
| 5.17 | CH | OCH₃ | O | Me | Δ | Cl | Cl | 1 | |
| 5.18 | CH | OCH₃ | O | Me | Me | Br | Br | 1 | foam |
| 5.19 | CH | OCH₃ | O | H | Me | Br | Br | 1 | |
| 5.20 | CH | OCH₃ | O | Me | Me | Cl | Cl | 2 | |
| 5.21 | CH | OCH₃ | O | H | Me | Cl | Cl | 2 | |
| 5.22 | CH | OCH₃ | O | Me | Me | F | F | 2 | |
| 5.23 | N | OCH₃ | NMe | Me | Me | Cl | Cl | 1 | |
| 5.24 | N | OCH₃ | NMe | H | Me | Cl | Cl | 1 | |
| 5.25 | N | OCH₃ | NMe | Me | Me | F | F | 1 | |
| 5.26 | N | OCH₃ | NMe | Me | Et | F | F | 1 | |
| 5.27 | N | OCH₃ | NMe | Me | | Br | Br | 1 | |
| 5.28 | N | OCH₃ | NPh | Me | Me | Cl | Cl | 1 | |
| 5.29 | N | OCH₃ | NPh | H | Me | Cl | Cl | 1 | |
| 5.30 | N | OCH₃ | NPh | Me | Et | Cl | Cl | 1 | |
| 5.31 | N | OCH₃ | O | Me | Me | Cl | Cl | 1 | |
| 5.32 | N | OCH₃ | O | H | Me | Cl | Cl | 1 | |
| 5.33 | N | OCH₃ | O | Me | Me | F | F | 1 | |
| 5.34 | N | OCH₃ | O | H | Me | F | F | 1 | |
| 5.35 | N | OCH₃ | O | Me | H | F | F | 1 | |
| 5.36 | N | OCH₃ | O | Me | C₃H₇ | Cl | Cl | 1 | |
| 5.37 | N | OCH₃ | O | Me | Δ | Cl | Cl | 1 | |
| 5.38 | N | OCH₃ | O | Δ | Me | Cl | Cl | 1 | |
| 5.39 | N | OCH₃ | O | Me | Δ | Cl | Cl | 1 | |
| 5.40 | N | OCH₃ | O | Me | Me | Br | Br | 1 | |
| 5.41 | N | OCH₃ | O | H | Me | Br | Br | 1 | |
| 5.42 | N | OCH₃ | O | Me | Me | Cl | Cl | 2 | |
| 5.43 | N | OCH₃ | O | H | Me | Cl | Cl | 2 | |
| 5.44 | N | OCH₃ | O | Me | Me | F | F | 2 | |
| 5.45 | N | NHCH₃ | NMe | Me | Me | Cl | Cl | 1 | |
| 5.46 | N | NHCH₃ | NMe | H | Me | Cl | Cl | 1 | |
| 5.47 | N | NHCH₃ | NMe | Me | Me | F | F | 1 | |
| 5.48 | N | NHCH₃ | NMe | Me | Et | F | F | 1 | |
| 5.49 | N | NHCH₃ | NMe | Me | | Br | Br | 1 | |
| 5.50 | CH | OCH₃ | O | Me | Me | H | H | 1 | isom.1: oil isom.2: oil |
| 5.51 | N | OCH₃ | O | Me | Me | Cl | Cl | 1 | isom.1: oil |
| 5.52 | N | NHCH₃ | O | Me | Me | Cl | Cl | 1 | 137–139° C. |
| 5.53 | N | NHCH₃ | O | Me | Me | Cl | Cl | 1 | |
| 5.54 | N | NHCH₃ | O | H | Me | Cl | Cl | 1 | |
| 5.55 | N | NHCH₃ | O | Me | Me | F | F | 1 | |
| 5.56 | N | NHCH₃ | O | H | Me | F | F | 1 | |
| 5.57 | N | NHCH₃ | O | Me | H | F | F | 1 | |
| 5.58 | N | NHCH₃ | O | Me | Me | Cl | Cl | 2 | |

TABLE 5-continued
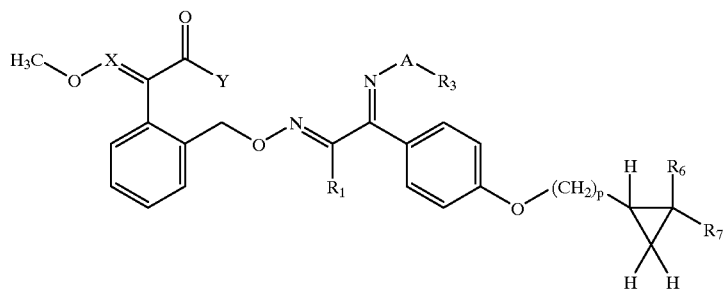
| Ex. No. | X | Y | A | $R_1$ | $R_3$ | $R_6$ | $R_7$ | p | Physical data |
|---|---|---|---|---|---|---|---|---|---|
| 5.59 | N | $NHCH_3$ | O | H | Me | Cl | Cl | 2 | |
| 5.60 | N | $NHCH_3$ | O | Me | Me | F | F | 2 | |
and the compounds
5.61
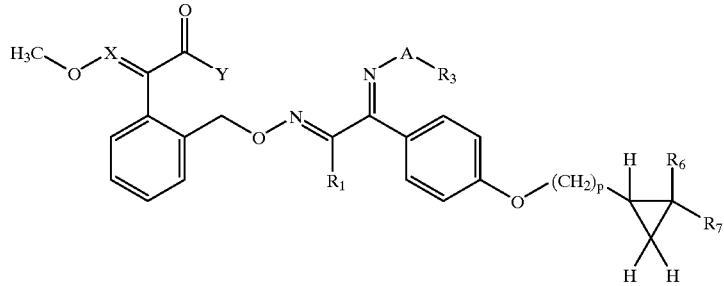
isomer 1: 113–115° C./isomer 2: oil
5.62
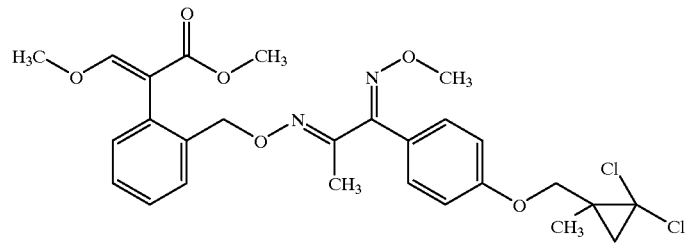
isomer 1: oil/isomer 2: oil
5.63
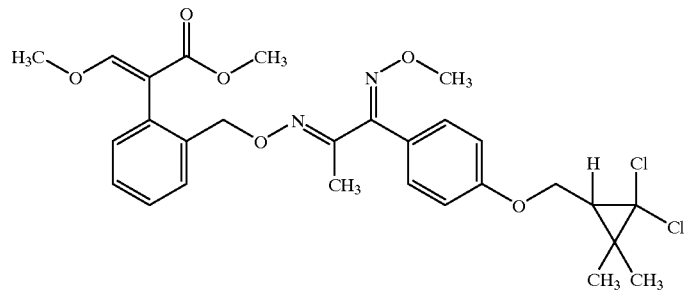
resin
5.64
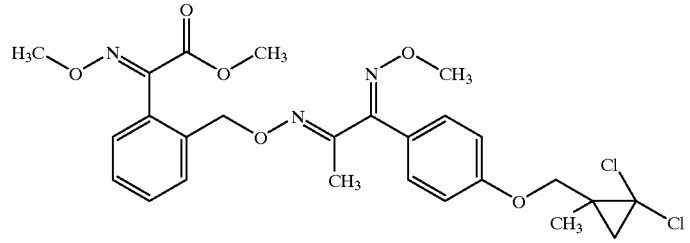
155–160° C.

TABLE 5-continued

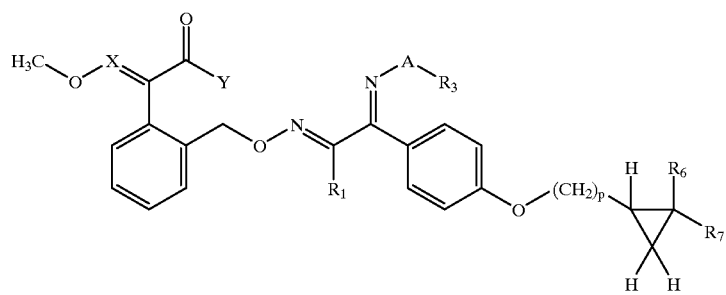

| Ex. No. | X | Y | A | R₁ | R₃ | R₆ | R₇ | p | Physical data |
|---|---|---|---|---|---|---|---|---|---|

5.65

[structure shown]

isomer 1: 109–110° C./isomer 2: resin 5.66

[structure shown]

isomer 1: 131–133° C./isomer 2: resin

**Physical data: m.p. or ¹H NMR of $R_1/R_2$ or $R_3$

TABLE 6

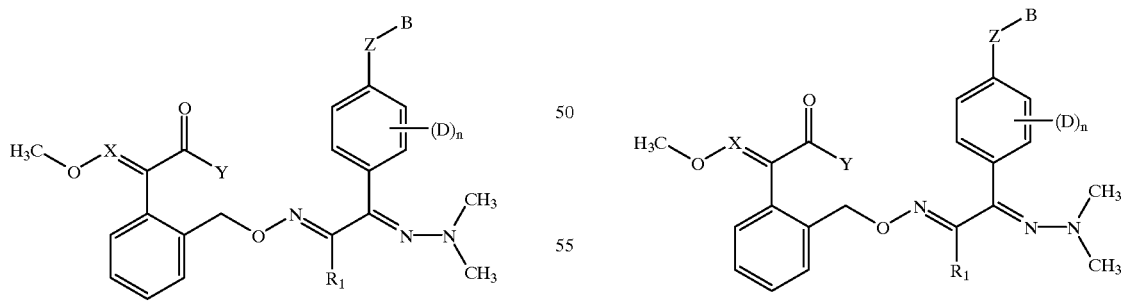

| Ex. | X | Y | $R_1$ | $Z^*$ | n | B or D | Physical data** |
|---|---|---|---|---|---|---|---|
| 6.1 | CH | OCH₃ | Me | O | 0 | allyl | oil |
| 6.2 | CH | OCH₃ | Me | — | 1 | 4-Br | isom.1: oil isom.2: oil |
| 6.3 | N | OCH₃ | Me | O | 0 | allyl | oil |
| 6.4 | N | OCH₃ | Me | — | 1 | 4-Br | 131–132° C. |
| 6.5 | N | NHCH₃ | Me | O | — | allyl | oil |
| 6.6 | N | NHCH₃ | Me | — | 1 | 4-Br | isom.1: 117–119° C. isom.2: oil |
| 6.7 | CH | OCH₃ | Me | — | 1 | 4-methyl- | isomer 1: 2.10 isomer 2: 2.08 |
| 6.8 | N | OCH₃ | Me | — | 1 | 4-methyl- | |
| 6.9 | N | NHCH₃ | Me | — | 1 | 4-methyl- | |

TABLE 7

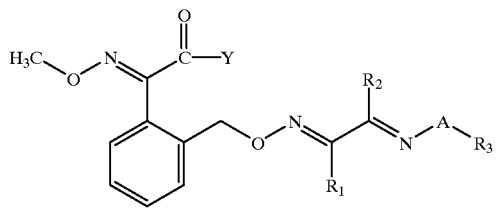

| Ex. No. | Y | A | $R_1$ | $R_2$ | $R_3$ or $NR_3R_4$ | Physical d.** |
|---|---|---|---|---|---|---|
| 7.1 | OEt | NMe | Me | Me | Me | |
| 7.2 | OEt | NMe | H | Me | 6-$CF_3$-2-pyridyl | |
| 7.3 | OEt | NMe | Me | Δ | 6-$CF_3$-2-pyridyl | |
| 7.4 | OEt | NMe | Me | H | phenyl | |
| 7.5 | OEt | NMe | Me | Me | phenyl | |
| 7.6 | OEt | NMe | Δ | Me | phenyl | |
| 7.7 | OEt | NMe | H | Me | 4-morpholinyl | |
| 7.8 | OEt | NPh | H | Me | phenyl | |
| 7.9 | OEt | NPh | Me | Me | phenyl | |
| 7.10 | OEt | NPh | Me | Δ | phenyl | |
| 7.11 | OEt | NPh | Δ | Me | phenyl | |
| 7.12 | OEt | O | Me | Me | Me | 75° C. |
| 7.13 | OEt | O | H | Me | Me | |
| 7.14 | OEt | O | Δ | Me | Me | |
| 7.15 | OEt | O | Me | Δ | Me | |
| 7.16 | OEt | O | Me | H | Me | |
| 7.17 | OEt | O | Me | Me | phenyl | |
| 7.18 | OEt | O | Me | Me | benzyl | |
| 7.19 | OEt | O | Me | Me | 3-$CF_3$-2-pyridyl | |
| 7.20 | OEt | O | Me | Me | 3-$CF_3$-phenyl | |
| 7.21 | $NH_2$ | NMe | Me | Δ | 3-$CF_3$-phenyl | |
| 7.22 | $NH_2$ | NMe | H | Me | 4-$CF_3$-phenyl | |
| 7.23 | $NH_2$ | NMe | Me | Me | 4-$CF_3$-phenyl | |
| 7.24 | $NH_2$ | NMe | Me | Me | 2-chlorophenyl | |
| 7.25 | $NH_2$ | NMe | Me | Me | 3-chlorophenyl | |
| 7.26 | $NH_2$ | NMe | Me | Me | 4-chlorophenyl | |
| 7.27 | $NH_2$ | O | Me | Me | phenyl | |
| 7.28 | $NH_2$ | O | Me | Me | Me | |
| 7.29 | $NH_2$ | O | Me | Me | benzyl | |
| 7.30 | $NH_2$ | O | Me | Me | Et | |
| 7.31 | $NH_2$ | O | H | Me | Et | |
| 7.32 | $NH_2$ | O | Δ | Me | Et | |
| 7.33 | $NH_2$ | O | Me | Δ | Et | |
| 7.34 | $NH_2$ | O | Me | H | Et | |
| 7.35 | $NH_2$ | O | Me | Me | methoxymethyl | |
| 7.36 | $NH_2$ | O | Me | Δ | methoxymethyl | |
| 7.37 | $NH_2$ | O | Δ | Me | methoxymethyl | |
| 7.38 | $NH_2$ | O | Me | Me | ethoxymethyl | |
| 7.39 | $NH_2$ | O | H | Me | propargyl | |
| 7.40 | $NH_2$ | O | Me | Me | cyanomethyl | |
| 7.41 | $NH_2$ | O | Me | Me | H | |
| 7.42 | $NH_2$ | O | Me | Me | $CF_3CH_2$ | |
| 7.43 | $NH_2$ | O | Δ | Me | $CF_3CH_2$ | |
| 7.44 | $NH_2$ | O | Me | H | $CF_3CH_2$ | |
| 7.45 | $NH_2$ | O | Me | H | $CF_3CH_2CH_2$ | |
| 7.46 | $NH_2$ | O | Me | Me | $CF_3CH_2CH_2$ | |
| 7.47 | $NH_2$ | O | Me | Me | $CF_3CH_2CH_2CH_2$ | |
| 7.48 | $NH_2$ | O | Δ | Me | $CF_3CH_2CH_2CH_2$ | |
| 7.49 | NHEt | NMe | Me | Δ | 3-$CF_3$-phenyl | |
| 7.50 | NHEt | NMe | H | Me | 4-$CF_3$-phenyl | |
| 7.51 | NHEt | NMe | Me | Me | 4-$CF_3$-phenyl | |
| 7.52 | NHEt | NMe | Me | Me | 2-chlorophenyl | |
| 7.53 | NHEt | NMe | Me | Me | 3-chlorophenyl | |
| 7.54 | NHEt | NMe | Me | Me | 4-chlorophenyl | |
| 7.55 | NHEt | O | Me | Me | phenyl | |
| 7.56 | NHEt | O | Me | Me | Me | 77° C. |
| 7.57 | NHEt | O | Me | Me | benzyl | |
| 7.58 | NHEt | O | Me | Me | Et | |
| 7.59 | NHEt | O | H | Me | Et | |
| 7.60 | NHEt | O | Δ | Me | Et | |
| 7.61 | NHEt | O | Me | Δ | Et | |
| 7.62 | NHEt | O | Me | H | Et | |
| 7.63 | NHEt | O | Me | Me | methoxymethyl | |
| 7.64 | NHEt | O | Me | Δ | methoxymethyl | |

TABLE 7-continued

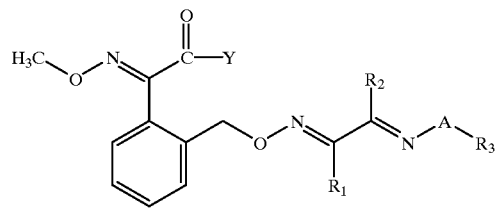

| Ex. No. | Y | A | $R_1$ | $R_2$ | $R_3$ or $NR_3R_4$ | Physical d.** |
|---|---|---|---|---|---|---|
| 7.65 | NHEt | O | Δ | Me | methoxymethyl | |
| 7.66 | NHEt | O | Me | Me | ethoxymethyl | |
| 7.67 | NHEt | O | H | Me | propargyl | |
| 7.68 | NHEt | O | Me | Me | cyanomethyl | |
| 7.69 | NHEt | O | Me | Me | H | |
| 7.70 | NHEt | O | Me | Me | $CF_3CH_2$ | |
| 7.71 | NHEt | O | Δ | Me | $CF_3CH_2$ | |
| 7.72 | NHEt | O | Me | H | $CF_3CH_2$ | |
| 7.73 | NHEt | O | Me | H | $CF_3CH_2CH_2$ | |
| 7.74 | NHEt | O | Me | Me | $CF_3CH_2CH_2$ | |
| 7.75 | NHEt | O | Me | Me | $CF_3CH_2CH_2CH_2$ | |
| 7.76 | NHEt | O | Δ | Me | $CF_3CH_2CH_2CH_2$ | |
| 7.77 | $N(Me)_2$ | NMe | Me | Δ | 3-$CF_3$-phenyl | |
| 7.78 | $N(Me)_2$ | NMe | H | Me | 4-$CF_3$-phenyl | |
| 7.79 | $N(Me)_2$ | NMe | Me | Me | 4-$CF_3$-phenyl | |
| 7.80 | $N(Me)_2$ | NMe | Me | Me | 2-chlorophenyl | |
| 7.81 | $N(Me)_2$ | NMe | Me | Me | 3-chlorophenyl | |
| 7.82 | $N(Me)_2$ | NMe | Me | Me | 4-chlorophenyl | |
| 7.83 | $N(Me)_2$ | O | Me | Me | phenyl | |
| 7.84 | $N(Me)_2$ | O | Me | Me | Me | |
| 7.85 | $N(Me)_2$ | O | Me | Me | benzyl | |
| 7.86 | $N(Me)_2$ | O | Me | Me | Et | |
| 7.87 | $N(Me)_2$ | O | H | Me | Et | |
| 7.88 | $N(Me)_2$ | O | Δ | Me | Et | |
| 7.89 | $N(Me)_2$ | O | Me | Δ | Et | |
| 7.90 | $N(Me)_2$ | O | Me | H | Et | |
| 7.91 | $N(Me)_2$ | O | Me | Me | methoxymethyl | |
| 7.92 | $N(Me)_2$ | O | Me | Δ | methoxymethyl | |
| 7.93 | $N(Me)_2$ | O | Δ | Me | methoxymethyl | |
| 7.94 | $N(Me)_2$ | O | Me | Me | ethoxymethyl | |
| 7.95 | $N(Me)_2$ | O | H | Me | propargyl | |
| 7.96 | $N(Me)_2$ | O | Me | Me | cyanomethyl | |
| 7.97 | $N(Me)_2$ | O | Me | Me | H | |
| 7.98 | $N(Me)_2$ | O | Me | Me | $CF_3CH_2$ | |
| 7.99 | $N(Me)_2$ | O | Δ | Me | $CF_3CH_2$ | |
| 7.100 | $N(Me)_2$ | O | Me | H | $CF_3CH_2$ | |
| 7.101 | $N(Me)_2$ | O | Me | H | $CF_3CH_2CH_2$ | |
| 7.102 | $N(Me)_2$ | O | Me | Me | $CF_3CH_2CH_2$ | |
| 7.103 | $N(Me)_2$ | O | Me | Me | $CF_3CH_2CH_2CH_2$ | |
| 7.104 | $N(Me)_2$ | O | Δ | Me | $CF_3CH_2CH_2CH_2$ | |

TABLE 8

(Intermediates)

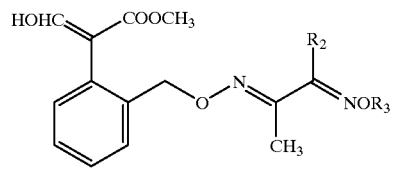

VII.1

| Ex. No. | $R_2$ | $R_3$ | $^1$H-NMR:δ(ppm) of the hydroxyl group |
|---|---|---|---|
| 8.1(H-8) | $CH_3$ | $CH_3$ | 12.00 |
| 8.2 | $CH_3$ | $CH_2$-cyclopropyl | 11.95 |
| 8.3 | $CH_3$ | $CH_2CH_2F$ | 11.95 |
| 8.4 | $CH_3$ | $CH_2CH=CH_2$ | 11.95 |
| 8.5 | $CH_3$ | $CH_2CF_3$ | 12.00 |

TABLE 8-continued (Intermediates)

VII.1

| Ex. No. | $R_2$ | $R_3$ | $^1$H-NMR:δ(ppm) of the hydroxyl group |
|---|---|---|---|
| 8.6 | 4-ethoxyphenyl | $CH_3$ | 11.90 (isomer I) |
|  |  |  | 11.95 (isomer II) |
| 8.7 | 4-allyloxyphenyl | $CH_3$ | 11.85 (isomer I) |
|  |  |  | 9.57 (isomer II) |

TABLE 9

(Intermediates)

VII.2

| Ex. No. | $R_2$ | $R_3$ | Phys. data |
|---|---|---|---|
| 9.1(H-10) | $CH_3$ | $CH_3$ | m.p. 78–81° C. |
| 9.2 | $CH_3$ | $CH_2$-cyclopropyl |  |
| 9.3 | $CH_3$ | $CH_2CH_2F$ |  |
| 9.4 | $CH_3$ | $CH_2CH=CH_2$ |  |
| 9.5 | $CH_3$ | $CH_2CF_3$ |  |
| 9.6 | 4-ethoxyphenyl | $CH_3$ |  |
| 9.7 | 4-allyloxyphenyl | $CH_3$ |  |

TABLE 10

(Intermediates)

VIII

| Ex. No. | $R_2$ | $R_3$ | $^1$H-NMR:δ(ppm) of $CH_3$*/$R_2$ |
|---|---|---|---|
| 10.1(H-7) | $CH_3$ | $CH_3$ | 1.98/2.01 |
| 10.2 | $CH_3$ | $CH_2$-cyclopropyl | 2.02/2.02 |
| 10.3 | $CH_3$ | $CH_2CH_2F$ | 2.00/2.05 |
| 10.4 | $CH_3$ | $CH_2CH=CH_2$ | 2.00/2.02 |
| 10.5 | $CH_3$ | $CH_2CF_3$ | 1.99/2.05 |
| 10.6 | 4-ethoxyphenyl | $CH_3$ | 2.06 ($CH_3$*) isomer I |
|  |  |  | 2.12 ($CH_3$*) isomer II |
| 10.7 | 4-allyloxyphenyl | $CH_3$ | 2.05 ($CH_3$*) isomer I |
|  |  |  | 2.11 ($CH_3$*) isomer II |
| 10.8 | 2-methylphenyl | $CH_3$ | 1.96 ($CH_3$*) |

TABLE 11

(Intermediates)

IX

| Ex. No. | $R_2$ | $R_3$ | Phys. data |
|---|---|---|---|
| 11.1 (H-9) | $CH_3$ | $CH_3$ | m.p. 81–83° C. |
| 11.2 | $CH_3$ | $CH_2$-cyclopropyl |  |
| 11.3 | $CH_3$ | $CH_2CH_2F$ |  |
| 11.4 | $CH_3$ | $CH_2CH=CH_2$ |  |
| 11.5 | $CH_3$ | $CH_2CF_3$ |  |
| 11.6 | 4-ethoxyphenyl | $CH_3$ |  |
| 11.7 | 4-allyloxyphenyl | $CH_3$ |  |
| 11.8 | 2-methylphenyl | $CH_3$ |  |

TABLE 12

(Intermediates)

II

| Ex. No. | $R_2$ | $R_3$ | Phys. data |
|---|---|---|---|
| 12.1 (in H-3) | 4-Methylphenyl | $CH_3$ | m.p.156–157° C. |
| 12.2(H-6,comp.AA) | (dichlorocyclopropylmethoxy-4-methylphenyl) | $CH_3$ | m.p.83–85° C. |

2. Formulation Examples of Active Ingredients of the Formula I (%=percent by Weight)

| 2.1. Wettable powders | a) | b) | c) |
|---|---|---|---|
| Active ingredient of Table 1-7 | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives, and the mixture is ground thoroughly in a suitable mill. This gives wettable powders which can be diluted with water to give suspensions of any desired concentration.

| 2.2. Emulsion concentrate | |
|---|---|
| Active ingredient of Table 1-7 | 10% |
| Octylphenol polyethylene glycol ether (4–5 mol of ethylene oxide) | 3% |
| Calcium dodecylbenzenesulfonate | 3% |
| Cyclohexanone | 34% |
| Xylene mixture | 50% |

Emulsions of any desired dilution can be prepared from this concentrate by diluting it with water.

| 2.3. Dusts | a) | b) |
|---|---|---|
| Active ingredient of Table 1-7 | 5% | 8% |
| Talc | 95% | — |
| Kaolin | — | 92% |

Ready-to-use dusts are obtained by mixing the active ingredient with the carrier and grinding the mixture in a suitable mill.

| 2.4. Extruder granules | |
|---|---|
| Active ingredient of Table 1-7 | 10% |
| Sodium lignosulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| 2.5. Coated granules | |
|---|---|
| Active ingredient of Table 1-7 | 3% |
| Polyethylene glycol (MW 200) | 3% |
| Kaolin | 94% |
| (MW = molecular weight) | |

In a mixer, the finely ground active ingredient is applied uniformly to the kaolin which has been moistened with polyethylene glycol. This gives dust-free coated granules.

| 2.6. Suspension concentrate | |
|---|---|
| Active ingredient of Table 1-7 | 40% |
| Ethylene glycol | 10% |
| Nonylphenol polyethylene glycol ether (15 mol of ethylene oxid) | 6% |
| Sodium lignosulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired dilution can be prepared by diluting it with water.

3. Biological Examples

A) Microbicidal Action

Example B-1: Action against *Phytophthora Infestans* on Tomatoes a) Curative Action Tomato plants cv. "Roter Gnom" are grown for three weeks and then sprayed with a zoospore suspension of the fungus and incubated in a cabinet at 18 to 20° and saturated atmospheric humidity. The humidification is interrupted after 24 hours. After the plants have dried, they are sprayed with a mixture which comprises the active ingredient, formulated as a wettable powder, at a concentration of 200 ppm. After the spray coating has dried, the plants are returned to the humid chamber for 4 days. Number and size of the typical leaf spots which have developed after this period are used to assess the activity of the test substances.

b) Preventive-systemic Action

The active ingredient, formulated as a wettable powder, is applied at a concentration of 60 ppm (relative to the soil volume) to the soil surface of three-week old tomato plants cv. "Roter Gnom" in pots. After the plants have been left to stand for three days, the underside of the leaves is sprayed with a zoospore suspension of *Phytophthora infestans*. The plants are then kept for 5 days in a spray cabinet at 18 to 20° C. and saturated atmospheric humidity. After this period, typical leaf spots develop, whose number and size are used for assessing the activity of the test substances.

While untreated, but infected, control plants show an infestation of 100%, the active ingredients of the formula I in accordance with one of the tables, in particular the compounds No. 1.5, 1.24, 1.117, 2.24, 2.74 and 3.24, allow the infestation in both tests to be reduced to 20% or less.

Example B-2: Action against *Plasmopara Viticola* (Bert et Curt) (Berl. et De Toni) on Vines a) Residual-preventive Action Vine cuttings cv. "Chasselas" are grown in the greenhouse. When they have reached the 10-leaf stage, 3 plants are sprayed with a mixture (200 ppm of active ingredient). After the spray coating on the plants has dried, the leaf underside is inoculated uniformly with a spore suspension of the fungus. The plants are subsequently kept in a humid chamber for 8 days. After this period, the disease symptoms of the control plants are clearly developed. Number and size of the lesions on the treated plants are used to assess the activity of the test substances.

b) Curative Action

Grape cuttings cv. "Chasselas" are grown in the greenhouse and, when they have reached the 10-leaf stage, are inoculated on the underside of the leaves with a spore suspension of Plasmopara viticola After the plants have remained for 24 hours in a humid cabinet, they are sprayed with a mixture of active ingredient (200 ppm of active ingredient). The plants are subsequently kept for 7 more days in the humid cabinet. After this period, the disease symptoms have developed on the control plants. Number and size of the lesions on the treated plants are used to assess the activity of the test substances.

In comparison with the control plants, the infestation of plants which have been treated with active ingredients of the formula I is 20% or less.

Example B-3: Action against *Pythium Debaryanum* on Sugar Beet (*Beta Vulgaris*)

a) Action after Soil Application

The fungus is grown on sterile oat grains and added to a mixture of soil and sand. This inoculated soil is filled into flower pots and sugar beet seeds are sown. Immediately after sowing, the test preparations, formulated as wettable powders, are poured over the soil in the form of an aqueous suspension (20 ppm of active ingredient relative to the soil volume). Thereupon, the pots are placed in a greenhouse for 2–3 weeks at 20–24° C. All the time, the soil is kept uniformly moist by spraying it gently with water. When the test is evaluated, the emergence of the sugar beet plants and the proportion of healthy and diseased plants is determined.
b) Action After Seed-dressineg The fungus is grown on sterile oat grains and added to a mixture of soil and sand. This inoculated soil is filled into flower pots and sugar beet seeds which have been dressed with the test preparations, formulated as seed-dressing powders (1000 ppm of active ingredient relative to the weight of the seeds), are sown. The pots together with the seeds are placed in a greenhouse at 20–24° C. for 2–3 weeks. The soil is kept uniformly moist by gently spraying it with water. When the test is evaluated, the emergence of the sugar beet plants and the proportion of healthy and diseased plants is determined. After treatment with active ingredients of the formula I, in particular with the compounds No. 1.5, 1.24, 1.117, 2.24, 2.74 and 3.24, over 80% of the plants emerge and have a healthy appearance. In the control pots, only few plants of unhealthy appearance have emerged.

Example B4: Residual-protective Action Against *Cercospora Arachidicola* on Groundnuts Groundnut plants 10 to 15 cm high are sprayed to drip point with an aqueous spray mixture (0.02% of active ingredient) and, 48 hours later, inoculated with a conidia suspension of the fungus. The plants are incubated for 72 hours at 21° and high atmospheric humidity and subsequently placed in a greenhouse until the typical leaf spots have developed. The action of the active ingredient is assessed 12 days after the inoculation on the basis of the number and size of the leaf spots.

Active ingredients of the formula I cause a reduction in leaf spots to less than approximately 10% of the leaf surface area In some cases, the disease is reduced completely (0–5% infestation).

Example B-5: Action Against *Puccinia Graminis* on Wheat a) Residual-protective Action 6 days after sowing, wheat plants are sprayed to drip point with an aqueous spray mixture (0.02% of active ingredient) and, 24 hours later, inoculated with a ureidospore suspension of the fungus. After an incubation time of 48 hours (conditions: relative humidity of 95 to 100% at 20°), the plants are placed in a greenhouse at 22°. 12 days after the inoculation, the development of rust pustules is assessed.
b) Systemic Action 5 days after sowing, an aqueous spray mixture (0.006% of active ingredient relative to the soil volume) is poured next to wheat plants. Any contact of the spray mixture with aerial parts of the plants is carefully avoided. 48 hours later, the plants are inoculated with a ureidospore suspension of the fungus. After an incubation time of 48 hours (conditions: relative humidity of 95 to 100% at 20°), the plants are placed in a greenhouse at 22°. 12 days after the inoculation, the development of rust pustules is assessed.

Compounds of the formula I, in particular those of Table 1, in particular No. 1.5, 1.24, 1.117, 2.74, cause a marked reduction in fungus infestation, in some cases down to 10–0%.

Example B-6: Action Against *Pyricularia Oryzae* on Rice a) Residual-protective Action Rice plants are grown for two weeks and then sprayed to drip point with an aqueous spray mixture (0.02% of active ingredient), and, 48 hours later, inoculated with a conidia suspension of the fungus. The fungus infestation is assessed 5 days after the inoculation, during which period the relative atmospheric humidity was kept at 95 to 100% and the temperature at 22°.
b) Systemic Action An aqueous spray mixture (0.006% of active ingredient relative to the soil volume) is poured next to 2-week old rice plants. Contact of the spray mixture with the aerial parts of the plants is carefully avoided. The pots are then filled with such an amount of water that the lowest parts of the stems of the rice plants are submerged. After 96 hours, the plants are inoculated with a conidia suspension of the fungus and kept for 5 days at a relative atmospheric humidity of 95 to 100% and a temperature of 24° C.

In many cases, compounds of the formula I prevent the development of disease on the infected plants.

Example B-7: Residual-protective Action Against *Venturia Inaequalis* on Apples

Apple cuttings having fresh shoots 10 to 20 cm in length are sprayed to drip point with a spray mixture (0.02% of active ingredient) and, 24 hours later, inoculated with a conidia suspension of the fungus. The plants are incubated for 5 days at a relative atmospheric humidity of 90 to 100% and kept in a greenhouse for a further 10 days at 20 to 24°. The infestation with scab was assessed 15 days after the inoculation.

Most of the compounds of the formula I of one of Tables 1, 2 or 3 have a sustainable action against scab diseases.

Example B-8: Action Against *Erysiphe Graminis* on Barley a) Residual-protective Action Barley plants approximately 8 cm high are sprayed to drip point with an aqueous spray mixture (0.02% of active ingredient) and, 3 to 4 hours later, dusted with conidia of the fungus. The inoculated plants are placed in a greenhouse at 22°. The fungus infestation is assessed 10 days after the inoculation.
b) Systemic Action An aqueous spray mixture (0.002% of active ingredient relative to the soil volume) is poured next to barley plants approximately 8 cm high. Contact of the spray mixture with aerial parts of the plants is carefully avoided. 48 hours later, the plants are dusted with conidia of the fungus. The inoculated plants are placed in a greenhouse at 22°. The fungus infestation is assessed 10 days after the inoculation.

Compounds of the formula I, in particular compounds No. 1.117, 2.24 and 3.24, are generally capable of reducing the disease to less than 20%, in some cases also completely.

Example B-9: Action Against *Podosphaera Leucotricha* on Apple Shoots Residual-protective Action Apple cuttings having fresh shoots approximately 15 cm long are sprayed with a spray mixture (0.06% of active ingredient). After 24 hours, the treated plants are inoculated with a conidia suspension of the fungus and placed in a controlled-environment cabinet at a relative atmospheric humidity of 70% and at 20° C. The fungus infestation is assessed 12 days after the inoculation.

Active ingredients of the formula I allow the disease to be reduced to less than 20%. Control plants show a disease level of 100%.

Example B-10: Action against *Botrytis Cinerea* on Apple Fruits. Residual—protective Action Artificially wounded apples are treated by applying dropwise a spray mixture (0.02% of active ingredient) to the wounds. The treated fruits are subsequently inoculated with a spore suspension of the fungus and incubated for one week at high atmospheric humidity and at approximately 20° C. The fungicidal action of the test substance is deduced from the number of wounds showing signs of rot Active ingredients of the formula I are capable of reducing the spread of rot, in some cases completely.

Example B-11: Action Against *Helminthosporium Gramineum*

Wheat grains are contaminated with a spore suspension of the fungus and allowed to dry. The contaminated grains are dressed with a suspension of the test substance (600 ppm of active ingredient relative to the weight of the seeds). After two days, the grains are arranged in suitable dishes containing agar, and, after a further four days, the development of fungal colonies around the grains is assessed. The test substance is assessed on the basis of the number and size of the fungal colonies.

A good action, i.e. inhibition of fungal colonies, is shown, in some cases, by compounds of the formula I.

Example B-12: Action Against *Colletotrichum Lapenarium* on Cucumbers

Cucumber plants are grown for two weeks and then sprayed with a spray mixture (concentration 0.002%). After 2 days, the plants are inoculated with a spore suspension ($1.5 \times 10^5$ spores/ml) of the fungus and incubated for 36 hours at 23° and high atmospheric humidity. The incubation is then continued at normal atmospheric humidity at approximately 22–23° C. The fungus infestation which has developed is assessed 8 days after the inoculation. Untreated, but infected, control plants show a fungus infestation of 100%.

A virtually complete inhibition of the infestation with disease is shown, in some cases, by compounds of the formula I, in particular by No. 1.5 and 3.24.

Example B-13: Action Against *Fusarium Nivale* on Rye

Rye cv. Tetrahell, naturally infected with *Fusarium nivale*, is dressed with the test fungicide using a mixing roller, the following concentrations being used: 20 or 6 ppm of a.i. (relative to the weight of the seed).

Using a seed drill, the infected and treated rye is drilled in October in a field in 3 m plots of 6 seed furrows. 3 replicates per concentration.

Until the infestation is evaluated, the test plants are grown under normal field conditions (preferably in a region with a complete covering of snow during the winter months).

To assess the phytotoxicity, seed emergence is scored in autumn and number of plants per unit area/number of tillers per plant in spring.

To determine the activity of the active ingredient, the percentage of Fusarium-infested plants is counted immediately after the snow has melted. In the present case, the number of infested plants was lower than 5%. The plants which emerged had a healthy appearance.

Example B-14: Action Against *Septoria Nodorum* on Wheat

Wheat plants in the 3-leaf stage are sprayed with a spray mixture (60 ppm of a.i.) prepared with a wettable powder of the active ingredients (2.8:1).

After 24 hours the treated plants are inoculated with a conidia suspension of the fungus. The plants are subsequently incubated for 2 days at a relative atmospheric humidity of 90–100 % and placed in a greenhouse at 20–24° C. for a further 10 days. 13 days after the inoculation, the fungus infestation is assessed. Less than 1% of the wheat plants were infested.

Example B-15: Action Against *Rhizoctonia Solani* on Rice Protective-local Soil Application The soil around 10-day old rice plants was watered with a suspension (spray mixture) prepared with a formulated test substance without aerial parts of the plants coming into contact with the suspension. Three days later, the plants were inoculated by placing a stem of barley straw infected with *Rhizoctonia solani* between the rice plants of each pot. After incubation for 6 days in a controlled-environment cabinet at 29° C. day-time and 26° C. night-time temperature and a relative atmospheric humidity of 95%, the fungus infestation is assessed. Fewer than 5% of the rice plants are infested. The plants had a healthy appearance.

Protective-local Follar Application 12-day old rice plants are sprayed with a suspension prepared with formulated test substances. One day later, inoculation is carried out by placing a stem of barley straw, infected with *Rhizoctonia solani*, between the rice plants of each pot The plants were scored after incubation for 6 days in a controlled-environment cabinet at 29° C. day-time and 26° C. night-time temperature and a relative atmospheric humidity of 95%. Unmated, but inoculated, control plants showed a fungal infestation of 100%. Compounds of the formula I cause in some cases complete inhibition of the infestation with disease.

B. Insecticidal Action

Example B-16: Action Against *Aphis Craccivora*

Pea seedlings are populated with *Aphis craccivora*, subsequently sprayed with a spray mixture comprising 400 ppm of active ingredient and then incubated at 20°. The percentage reduction in population (% action) is determined after 3 and 6 days by comparing the number of dead aphids on the treated and the untreated plants. In this test, compounds of Tables 1–7 have a good action. Compound No. 4.5, isomer 1, in particular, has an action of over 80%.

Example B-17: Action Against *Diabrotica Balteata*

Maize seedlings are sprayed with an aqueous emulsion spray mixture comprising 400 ppm of active ingredient, then, after the spray coating has dried on, populated with 10 second instar larvae of *Diabrotica balteata* and subsequently placed in a plastic container. The percentage reduction in population (% action) is determined after 6 days by comparing the number of dead larvae of the treated and untreated plants.

In this test, compounds of Tables 1–7 have a good action. In particular, compounds No. 1.5, 1.24. 2.24, 3.24, 4.5, isomer 1, 4.14, isomer 1, 4.14, isomer 1, 4.117, both isomers, 4.121, 4.170, 5.9, isomer 1 and 5.51, isomer 1, have an action of over 80%

Example B-18: Action Against *Heliothis Virescens*

Young soya bean plants are sprayed with an aqueous emulsion spray mixture comprising 400 ppm of active ingredient, then, after the spray coating has dried on, populated with 10 first instar caterpillars of *Heliothis virescens* and subsequently placed in a plastic container. The percentage reduction in population and the feeding damage (% action) are determined after 6 days by comparing the number of dead caterpillars and the feeding damage of the treated and untreated plants.

In this test, compounds of Tables 1–7 show a good action. In particular, compounds No. 4.5, isomer 1, 4.14, isomer 1, 4.18, 4.117, both isomers, 4.121, 5.9, isomer 1, and 5.52, isomer 1, have an action of over 80%.

Example B-19: Action Against *Spodoptera Littoralis*

Young soya bean plants are sprayed with an aqueous emulsion spray mixture comprising 400 ppm of active ingredient, then, after the spray coating has dried on, populated with 10 third instar caterpillars of *Spodoptera littoralis* and subsequently placed in a plastic container. The percentage reduction in population and the percentage reduction in feeding damage (% action) are determined after 3 days by comparing the number of dead caterpillars and the feeding damage of the treated and untreated plants.

In this test, compounds of Tables 1–7 show a good action. In particular, compounds No. 1.5, 1.24. 2.24, 3.24, 4.18, 4.5, isomer 1, 5.9, isomer 1, and 5.52, isomer 1, have an action of over 80%.

C. Acaricidal Activity

Example B-20: Action Against *Tetranychus Urticae*

Young bean plants are populated with a mixed population of *Tetranychus urticae*, then, 1 day later, sprayed with an aqueous emulsion spray mixture comprising 400 ppm of active ingredient, incubated for 6 days at 25° and subsequently evaluated. The percentage reduction in population (% action) is determined by comparing the number of dead eggs, larvae and adults on the treated and untreated plants.

In this test, compounds of Tables 1–6 show a good action. In particular, compounds No. 1.5, 1.24 und 3.24, 4.5, isomer 1, 4.14, isomer 1, 4.117, both isomers, 5.9, isomer 1, and 5.52, isomer 1, have an action of over 80%.

Example B-21: Action Against *Boophilus Microplus*

Adult female ticks which have sucked themselves full are attached to a PVC board and covered with a cottonwool ball, and 10 ml of aqueous test solution comprising 125 ppm of active ingredient are poured over the ticks. The cottonwool ball is removed, and the ticks are incubated for 4 weeks for oviposition. The action becomes apparent either, in the case of the female, in the form of mortality or sterility or, in the case of the eggs, in the form of an ovicidal action.

What is claimed is:

1. A compound of the formula:

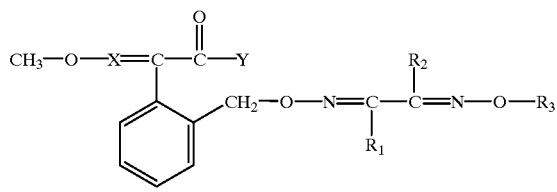

in which:
(a) X is N and Y is $OR_{11}$ or $N(R_{12})R_{13}$ where $R_{11}$ is $C_1$–$C_4$alkyl and $R_{12}$ and $R_{13}$, independently, are hydrogen or $C_1$–$C_4$alkyl, or (b) X is CH and Y is $OR_{11}$ where $R_{11}$ is $C_1$–$C_4$alkyl; $R_1$ is $C_1$–$C_4$alkyl, halo-$C_1$–$C_4$alkyl, cyclopropyl, cyano, or methylthio;

$R_2$ is hydrogen, $C_1$–$C_6$alkyl, or $C_3$–$C_6$cycloalkyl;

$R_3$ is hydrogen, $C_1$–$C_6$alkyl, $C_1$–$C_6$haloalkyl having 1 to 5 halogen atoms, $C_1$–$C_4$alkoxy-$C_1$–$C_2$alkyl, $C_2$–$C_4$alkenyl-$C_1$–$C_2$alkyl, which is unsubstituted or substituted by 1 to 3 halogen atoms, $C_2$–$C_4$alkynyl-$C_1$–$C_2$alkyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano-$C_1$–$C_4$alkyl, $C_1$–$C_4$alkoxycarbonyl-$C_1$–$C_2$alkyl, $C_1$–$C_4$alkoxycarbamoyl-$C_1$–$C_2$alkyl, phenyl-$C_1$–$C_3$alkyl which is unsubstituted or substituted with from 1 to 3 substituents independently selected from the group consisting of $C_1$–$C_3$alkyl, $C_1$–$C_4$alkoxy, halogen, $C_1$–$C_4$-haloalkyl having 1 to 3 halogen atoms, $C_1$–$C_4$alkylenedioxy, nitro and cyano, or phenyl which is unsubstituted or substituted with 1 or 2 substitutents independently selected from the group consisting of halogen, $C_1$–$C_4$alkyl, $C_1$–$C_4$alkoxy, $C_1$–$C_2$haloalkyl, cyano, and nitro; or an isomer or isomer mixture thereof.

2. A compound according to claim 1 in which X is N and Y is —$OCH_3$.

3. A compound according to claim 2 in which $R_1$ is methyl, cyclopropyl, or cyano.

4. A compound according to claim 1 in which X is CH and Y is —$OCH_3$.

5. A compound according to claim 4 in which $R_1$ is methyl, cyclopropyl, or cyano.

6. A compound according to claim 1 in which X is N and Y is $NHCH_3$.

7. A compound according to claim 6 in which $R_1$ is methyl, cyclopropyl, or cyano.

8. A compound according to claim 1 in which $R_2$ is hydrogen, $C_1$–$C_4$alkyl, or cyclopropyl.

9. A compound according to claim 8 in which $R_2$ is hydrogen, methyl, or cyclopropyl.

10. A compound according to claim 9 in which $R_3$ is hydrogen, $C_1$–$C_4$alkyl, cyclopropyl, or phenyl which is unsubstituted or substituted with 1 or 2 substituents independently selected from the group consisting of $C_1$–$C_3$alkyl, $C_1$–$C_4$alkoxy, halogen, $C_1$–$C_2$haloalkyl having 1 to 3 halogen atoms, nitro, and cyano.

11. A compound according to claim 1 in which (a) X is N and Y is methoxy, ethoxy, amino, methylamino, ethylamino, or dimethylamino, or (b) X is CH and Y is methoxy or ethoxy; $R_1$ is methyl or cyclopropyl; and $R_3$ is hydrogen, $C_1$–$C_6$alkyl, $C_1$–$C_3$haloalkyl, methoxymethyl, ethoxymethyl, propargyl, 2-chloroallyl, cyclopropylmethyl, dichlorocyclopropylmethyl, cyanomethyl, methoxycarbonylmethyl, phenyl$C_1$–$C_3$alkyl in which the phenyl group is unsubstituted or substituted with methyl, methoxy, fluoro, chloro, trifluoromethyl,methylenedioxy, nitro, or cyano.

12. The compound according to claim 1 which is methyl 3-methoxy-2-[2-(3-methoxyiminobut-2-yliminooxymethyl)phenyl]acrylate.

13. The compound according to claim 1 which is methyl 2-[2-(3-methoxyiminobut-2-yliminooxymethyl)phenyl]glyoxylate O-methyloxime.

14. The compound according to claim 1 which is methyl 2-{2-[3-(2,2,2-trifluoroethoxyimino)but-2-yliminooxymethyl]phenyl}glyoxylate O-methyloxime.

15. The compound according to claim 1 which is N-monomethyl 2-[2-(3-methoxyiminobut-2-yliminooxymethyl)phenyl]glyoxylamide O-methyloxime.

16. A composition for controlling pests, comprising, as active ingredient, a compound according to claim 1 together with a suitable carrier.

17. A method for controlling and preventing pests which comprises applying a compound according to claim 1 to the pests or their environment.

18. A compound of the formula:

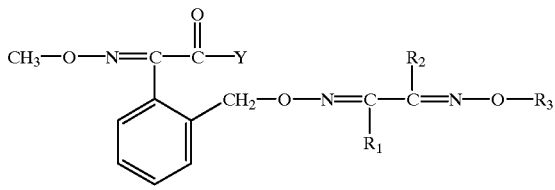

in which:

Y is $OR_{11}$ or $N(R_{12})R_{13}$;

$R_1$ is $C_1$–$C_4$alkyl, halo-$C_1$–$C_4$alkyl, cyclopropyl, cyano, or methylthio;

$R_2$ is phenyl which is unsubstituted or substituted with from 1 to 4 substituents independently selected from the group consisting of halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$-alkynyloxy, $C_1$–$C_4$alkylenedioxy, cyano, and nitro;

$R_3$ is hydrogen, $C_1$–$C_6$alkyl, $C_1$–$C_6$haloalkyl having 1 to 5 halogen atoms, $C_1$–$C_4$alkoxy-$C_1$–$C_2$alkyl, $C_2$–$C_4$alkenyl-$C_1$–$C_2$alkyl, which is unsubstituted or substituted by 1 to 3 halogen atoms, $C_2$–$C_4$alkynyl-$C_1$–$C_2$alkyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano$C_1$–$C_4$alkyl, $C_1$–$C_4$alkoxycarbonyl-$C_1$–$C_2$alkyl, $C_1$–$C_4$alkoxycarbamoyl-$C_1$–$C_2$alkyl, phenyl-$C_1$–$C_3$alkyl which is unsubstituted or substituted with from 1 to 3 substituents independently selected from the group consisting of $C_1$–$C_3$alkyl, $C_1$–$C_4$alkoxy, halogen, $C_1$–$C_4$haloalkyl having 1 to 3 halogen atoms, $C_1$–$C_4$alkylenedioxy, nitro and cyano, or phenyl which is unsubstituted or substituted with 1 or 2 substituents independently selected from the group consisting of halogen, $C_1$–$C_4$alkyl, $C_1$–$C_4$alkoxy, $C_1$–$C_2$haloalkyl, cyano, and nitro;

$R_{11}$ is $C_1$–$C_4$alkyl; and each of $R_{12}$ and $R_{13}$, independently of the other, is hydrogen or $C_1$–$C_4$alkyl; and an isomers or isomer mixture thereof.

19. A compound according to claim 18 in which Y is methylamino, and $R_1$ is methyl, cyclopropyl, or cyano.

20. A compound according to claim 18 in which Y is methylamino, and $R_2$ is phenyl which is unsubstituted or substituted with 1 or 2 substituents independently selected from the group consisting of chloro, fluoro, bromo, methyl, allyloxy, $C_1$–$C_4$alkoxy, trifluoromethyl, cyano, and nitro.

21. A compound according to claim 20 in which $R_1$ is methyl, cyclopropyl, or cyano; $R_2$ is methylphenyl, bromophenyl, chlorophenyl, fluorophenyl, methoxyphenyl, ethoxyphenyl, trifluoromethylphenyl, allyloxyphenyl, cyanophenyl, or nitrophenyl; $R_3$ is hydrogen, $C_1$–$C_6$alkyl, $C_1$–$C_3$haloalkyl, methoxymethyl, ethoxymethyl, propargyl, 2-chloroallyl, cyclopropylmethyl, dichlorocyclopropylmethyl, cyanomethyl, methoxycarbonylmethyl, phenyl$C_1$–$C_3$alkyl in which the phenyl group is unsubstituted or substituted with methyl, methoxy, fluoro, chloro, trifluoromethyl, methylenedioxy, nitro, or cyano; $R_{12}$ is hydrogen; and $R_{13}$ is methyl.

22. A composition for controlling pests, comprising, as active ingredient, a compound according to claim 18 together with a suitable carrier.

23. A method for controlling and preventing pests which comprises applying a compound according to claim 18 to the pests or their environment.

24. A compound of the formula:

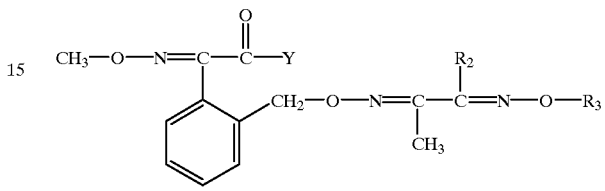

in which:

Y is methoxy or methylamino;

$R_2$ is methyl, phenyl which is unsubstituted or substituted with from 1 to 4 substituents independently selected from the group consisting of halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano, and nitro, or thienyl;

$R_3$ is $C_1$–$C_6$alkyl; or an isomer or isomer mixture thereof.

25. A compound according to claim 18 in which Y is methoxy, $R_1$ is methyl, cyclopropyl, or cyano.

26. A compound according to claim 18 in which Y is methoxy, $R_2$ is phenyl which is unsubstituted or substituted with 1 or 2 substituents independently selected from the group consisting of chloro, fluoro, bromo, methyl, allyloxy, $C_1$–$C_4$alkoxy, trifluoromethyl, cyano, and nitro.

27. A compound according to claim 26 in which $R_1$ is methyl, cyclopropyl, or cyano; $R_2$ is methylphenyl, bromophenyl, chlorophenyl, fluorophenyl, methoxyphenyl, ethoxyphenyl, trifluoromethylphenyl, allyloxyphenyl, cyanophenyl, or nitrophenyl; and $R_3$ is hydrogen, $C_1$–$C_6$alkyl, $C_1$–$C_3$haloalkyl, methoxymethyl, ethoxymethyl, propargyl, 2-chloroallyl, cyclopropylmethyl dichlorocyclopropylmethyl, cyanomethyl, methoxycarbonylmethyl, phenyl$C_1$–$C_3$alkyl in which the phenyl group is unsubstituted or substituted with methyl, methoxy, fluoro, chloro, trifluoromethyl, methylenedioxy, nitro, or cyano.

28. A compound according to claim 24 in which $R_3$ is $C_1$–$C_4$alkyl.

29. A compound according to claim 28 in which $R_2$ is methyl, methylphenyl, bromophenyl, chlorophenyl, fluorophenyl, methoxyphenyl, ethoxyphenyl, trifluoromethylphenyl, allyloxyphenyl, cyanophenyl, nitrophenyl, or thienyl.

30. A composition for controlling pests, comprising, as active ingredient, a compound according to claim 24 together with a suitable carrier.

31. A method for controlling and preventing pests which comprises applying a compound according to claim 24 to the pests or their environment.

32. A compound of the formula:

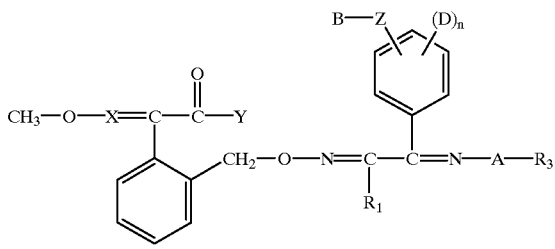

in which:
(a) X is N and Y is $OR_{11}$ or $N(R_{12})R_{13}$ where $R_{11}$ is $C_1$–$C_4$alkyl and $R_{12}$ and $R_{13}$, independently, are hydrogen or $C_1$–$C_4$alkyl, or
(b) X is CH and Y is $OR_{11}$ where $R_{11}$ is $C_1$–$C_4$alkyl;
$R_1$ is $C_1$–$C_4$alkyl, halo-$C_1$–$C_4$alkyl, cyclopropyl, cyano, or methylthio;
$R_3$ is hydrogen, $C_1$–$C_6$alkyl, $C_1$–$C_6$haloalkyl having 1 to 5 halogen atoms, $C_1$–$C_4$akoxy-$C_1$–$C_2$alkyl, $C_1$–$C_4$alkenyl-$C_1$–$C_2$alkyl, which is unsubstituted or substituted by 1 to 3 halogen atoms, $C_2$–$C_4$alkynyl-$C_1$–$C_2$alkyl, $C_3$–$C_6$cycloalkyl which is unsubstituted or substituted by 1 to 4 halogen atoms, $C_3$–$C_6$cycloalkyl-$C_1$–$C_4$alkyl which is unsubstituted or substituted by 1 to 4 halogen atoms, cyano$C_1$–$C_4$alkyl, $C_1$–$C_4$alkoxycarbonyl-$C_1$–$C_2$alkyl, $C_1$–$C_4$alkoxycarbamoyl-$C_1$–$C_2$alkyl, phenyl-$C_1$–$C_3$alkyl which is unsubstituted or substituted with from 1 to 3 substituents independently selected from the group consisting of $C_1$–$C_3$alkyl, $C_1$–$C_4$alkoxy, halogen, $C_1$–$C_4$-haloalkyl having 1 to 3 halogen atoms, $C_1$–$C_4$alkylenedioxy, nitro and cyano, or phenyl which is unsubstituted or substituted with 1 or 2 substitutents independently selected from the group consisting of halogen, $C_1$–$C_4$alkyl, $C_1$–$C_4$alkoxy, $C_1$–$C_2$haloalkyl, cyano, and nitro;
Z is —O—, —O($C_1$–$C_4$alkyl)—, —($C_1$–$C_4$alkyl)O—, —S(O)$_m$—, —($C_1$–$C_4$alkyl)S(O)$_m$—, or —S(O)$_m$($C_1$–$C_4$alkyl)— in which m is 0, 1, or 2;
B is $C_1$–$C_6$alkyl, $C_1$–$C_6$haloalkyl, $C_3$–$C_6$cycloalkyl, $C_2$–$C_6$alkenyl which is unsubstituted or substituted by 1 to 3 halogen atoms, $C_2$–$C_4$alkynyl-$C_1$–$C_2$alkyl which is unsubstituted or substituted by 1 to 3 halogen atoms, unsubstituted aryl, or unsubstituted heteroaryl;
D is the same or different halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano, or nitro;
n has a value of 0, 1, 2, 3, or 4; and
A is an O atom or $NR_4$;
$R_4$ is phenyl or $C_1$–$C_4$alkyl; or
an isomer or isomer mixture thereof.

33. A compound according to claim 32 in which Z is —O—, —O($C_1$–$C_4$alkyl)—, or —($C_1$–$C_4$alkyl)O— and B is unsubstituted phenyl.

34. A compound according to claim 32 in which (a) X is N and Y is methoxy, ethoxy, amino, methylamino, ethylamino, or dimethylamino or (b) X is CH and Y is methoxy or ethoxy; $R_1$ is methyl or cyclopropyl; $R_3$ is hydrogen, $C_1$–$C_6$alkyl, $C_1$–$C_3$haloalkyl, methoxymethyl, ethoxymethyl, propargyl, 2-chloroallyl, cyclopropylmethyl, dichlorocyclopropylmethyl, cyanomethyl, methoxycarbonylmethyl, phenyl$C_1$–$C_3$alkyl in which the phenyl group is unsubstituted or substituted with methyl, methoxy, fluoro, chloro, trifluoromethyl, methylenedioxy, nitro, or cyano; A is —O— or —$NR_4$ in which $R_4$ is phenyl or methyl; Z is —O—, —O($CH_2$)—, or —($CH_2$)O—; B is unsubstituted phenyl.

35. The compound according to claim 32 which is methyl 3-methoxy-2-[1-(4-methylphenyl)-1-(3-methoxyimino)prop-2-yliminooxymethyl)phenyl]acrylate.

36. The compound according to claim 32 which is methyl 3-methoxy-2-[1-(4-allyloxyphenyl)-1-(3-methoxyimino)prop-2-yliminooxymethyl)phenyl]acrylate.

37. The compound according to claim 32 which is methyl 3-methoxy-2-[1-(4-propargyloxyphenyl)-1-(3-methoxyimino)prop-2-yliminooxymethyl)phenyl]acrylate.

38. The compound according to claim 32 which is methyl 2-[1-(4-chlorophenyl)-1-(3-methoxyimino)-prop-2-yliminooxymethyl)phenyl]glyoxylate O-methyloxime.

39. The compound according to claim 32 which is methyl 2-[1-(3-chlorophenyl)-1-(3-methoxyimino)-prop-2-yliminooxymethyl)phenyl]glyoxylate O-methyloxime.

40. The compound according to claim 32 which is methyl 2-[1-(4-fluorophenyl)-1-(3-methoxyimino)-prop-2-yliminooxymethyl)phenyl]glyoxylate O-methyloxime.

41. The compound according to claim 32 which is methyl 2-[1-(4-ethoxyphenyl)-1-(3-methoxyimino)-prop-2-yliminooxymethyl)pheny]glyoxylate O-methyloxime.

42. The compound according to claim 32 which is N-monomethyl 2-[1-(4-chlorophenyl)-1-(3-methoxyimino)-prop-2-yliminooxymethyl)phenyl]glyoxylamide O-methyloxime.

43. The compound according to claim 32 which is N-monomethyl 2-[1-(4-methylphenyl)-1-(3-methoxyimino)-prop-2-yliminooxymethyl)phenyl]glyoxylamide O-methyloxime.

44. The compound according to claim 32 which is N-monomethyl 2-[1-(4-methoxyphenyl)-1-(3-methoxyimino)-prop-2-yliminooxymethyl)phenyl]glyoxylamide O-methyloxime.

45. The compound according to claim 32 which is N-monomethyl 2-[1-(4-fluorophenyl)-1-(3-methoxyimino)-prop-2-yliminooxymethyl)phenyl]glyoxyl-amide O-methyloxime.

46. The compound according to claim 32 which is N-monomethyl 2-[1-phenyl-1-(3-methoxyimino)-prop-2-yliminooxymethyl)phenyl]glyoxylamide O-methyloxime.

47. The compound according to claim 32 which is methyl 3-methoxy-2-[1-[4-(3-tri-fluoromethylbenzyloxy)phenyl]-1-(3-methoxyimino)prop-2-yliminooxymethyl)-phenyl]acrylate.

48. The compound according to claim 32 which is methyl 3-methoxy-2-{1-[4-(4-fluorobenzyloxy)phenyl]-1-(3-methoxyimino)prop-2-yliminooxymethyl)phenyl}acrylate.

49. The compound according to claim 32 which is methyl 3-methoxy-2-{1-[4-(3-tri-fluoromethylbenzylsulfonyl)phenyl]-1-(3-methoxyimino)prop-2-yliminooxymethyl)phenyl}acrylate.

50. The compound according to claim 32 which is methyl 3-methoxy-2-{1-[4-(2,2-dichlorocyclopropylmethoxy)phenyl]-1-(3-metboxyimino)prop-2-yliminooxymethyl)phenyl}acrylate.

51. The compound according to claim 32 which is methyl 2-{1-[4-(2,2-dichlorocyclopropylmethoxy)phenyl]-1-(3-methoxyimino)prop-2-yliminooxymethyl)phenyl}glyoxylate O-methyloxime.

52. The compound according to claim 32 which is N-monomethyl 2-{1-[4-(2,2-dichlorocyclopropylmethoxy)phenyl]-1-(3-methoxyimino)prop-2-yliminooxymethyl)phenyl}glyoxylamide O-methyloxime.

* * * * *